(12) United States Patent
Berrada et al.

(10) Patent No.: US 9,963,740 B2
(45) Date of Patent: May 8, 2018

(54) METHOD AND DEVICE FOR MARKING ARTICLES

(71) Applicant: APDN (B.V.I.) Inc., Tortola (VG)

(72) Inventors: Abdelkrim Berrada, Lake Ronkonkoma, NY (US); MingHwa Benjamin Liang, East Setauket, NY (US); Lawrence Jung, Forest Hills, NY (US)

(73) Assignee: APDN (B.V.I.), INC., Tortola (VG)

( * ) Notice: Subject to any disclaimer, the term of this patent is extended or adjusted under 35 U.S.C. 154(b) by 0 days. days.

(21) Appl. No.: 14/497,614

(22) Filed: Sep. 26, 2014

(65) Prior Publication Data

US 2015/0018538 A1     Jan. 15, 2015

Related U.S. Application Data

(63) Continuation-in-part of application No. 13/789,093, filed on Mar. 7, 2013.

(60) Provisional application No. 61/883,874, filed on Sep. 27, 2013.

(51) Int. Cl.
*C12Q 1/68* (2018.01)

(52) U.S. Cl.
CPC ......... *C12Q 1/6876* (2013.01); *C12Q 1/6816* (2013.01)

(58) Field of Classification Search
None
See application file for complete search history.

(56) References Cited

U.S. PATENT DOCUMENTS

| | | |
|---|---|---|
| 4,183,989 A | 1/1980 | Tooth |
| 4,278,557 A | 7/1981 | Elwell, Jr. |
| 4,454,171 A * | 6/1984 | Diggle, Jr. ............... D06C 5/00 26/80 |
| 4,548,955 A | 10/1985 | Okhata et al. |
| 4,683,195 A | 7/1987 | Mullis et al. |
| 4,683,202 A | 7/1987 | Mullis |
| 4,739,044 A | 4/1988 | Stabinsky |
| 4,757,141 A | 7/1988 | Fung et al. |
| 4,861,620 A | 8/1989 | Azuma et al. |

(Continued)

FOREIGN PATENT DOCUMENTS

| | | |
|---|---|---|
| EP | 0 477 220 B1 | 4/1992 |
| EP | 0 623 658 A2 | 11/1994 |

(Continued)

OTHER PUBLICATIONS

S. Hou, X. Li and X-Z Feng Method to improve DNA Condesation Efficiency by Alkali Treatment. Nucleosides, Nucleotides and Nucleic Acids, 2009. 28:725-735.Taylor & Francis Group, LLC.

(Continued)

*Primary Examiner* — Robert T. Crow
(74) *Attorney, Agent, or Firm* — Hoffmann & Baron, LLP

(57) ABSTRACT

Provided are a method and device for marking an article for security, tracking or authentication. The method includes depositing a solution comprising a nucleic acid marker onto at least a portion of the article. The nucleic acid marker may be activated, for example, by adding a functional group to the nucleic acid marker. The activation of the nucleic acid marker may be performed by exposure to alkaline conditions. The method is well suited for marking fibers and textiles, as well as many other items.

5 Claims, 13 Drawing Sheets

(56) References Cited

U.S. PATENT DOCUMENTS

| | | |
|---|---|---|
| 4,965,188 A | 10/1990 | Mullis et al. |
| 5,047,519 A | 9/1991 | Hobbs, Jr. et al. |
| 5,075,216 A | 12/1991 | Innis et al. |
| 5,089,691 A | 2/1992 | Morisaki et al. |
| 5,132,242 A | 7/1992 | Cheung |
| 5,139,812 A | 8/1992 | Lebacq |
| 5,151,507 A | 9/1992 | Hobbs, Jr. et al. |
| 5,156,765 A | 10/1992 | Smrt et al. |
| 5,176,203 A | 1/1993 | Larzul |
| 5,270,183 A | 12/1993 | Corbett et al. |
| 5,415,839 A | 5/1995 | Zaun et al. |
| 5,429,952 A | 7/1995 | Garner et al. |
| 5,451,505 A | 9/1995 | Dollinger |
| 5,498,283 A | 3/1996 | Botros et al. |
| 5,508,197 A | 4/1996 | Hansen et al. |
| 5,595,871 A | 1/1997 | DelVecchio et al. |
| 5,599,578 A | 2/1997 | Butland |
| 5,602,381 A | 2/1997 | Hoshino et al. |
| 5,639,603 A | 6/1997 | Dower et al. |
| 5,643,728 A | 7/1997 | Slater et al. |
| 5,736,314 A | 4/1998 | Hayes et al. |
| 5,763,176 A | 6/1998 | Slater et al. |
| 5,776,713 A | 7/1998 | Garner et al. |
| 5,849,208 A | 12/1998 | Hayes et al. |
| 5,866,336 A | 2/1999 | Nazarenko et al. |
| 5,912,257 A | 6/1999 | Prasad et al. |
| 5,942,444 A | 8/1999 | Rittenburg et al. |
| 5,977,436 A | 11/1999 | Thomas et al. |
| 5,989,823 A | 11/1999 | Jayasena et al. |
| 6,013,789 A | 1/2000 | Rampal |
| 6,030,657 A | 2/2000 | Butland et al. |
| 6,033,880 A | 3/2000 | Haff et al. |
| 6,057,370 A | 5/2000 | Weiland et al. |
| 6,127,120 A | 10/2000 | Graham et al. |
| 6,132,996 A | 10/2000 | Hunicke-Smith |
| 6,140,075 A | 10/2000 | Russell et al. |
| 6,169,174 B1 | 1/2001 | Hasegawa et al. |
| 6,261,809 B1 | 7/2001 | Bertling et al. |
| 6,287,768 B1 * | 9/2001 | Chenchik .......... B01J 19/0046 204/600 |
| 6,312,911 B1 | 11/2001 | Bancroft et al. |
| 6,326,489 B1 | 12/2001 | Church et al. |
| 6,342,359 B1 | 1/2002 | Lee et al. |
| 6,361,944 B1 | 3/2002 | Mirkin et al. |
| 6,379,897 B1 | 4/2002 | Weidenhammer et al. |
| 6,399,397 B1 | 6/2002 | Zarling et al. |
| 6,537,747 B1 | 3/2003 | Mills, Jr. et al. |
| 6,537,752 B1 | 3/2003 | Astle |
| 6,576,422 B1 | 6/2003 | Weinstein et al. |
| 6,608,228 B1 | 8/2003 | Cumpston et al. |
| 6,613,560 B1 | 9/2003 | Tso et al. |
| 6,632,653 B1 | 10/2003 | Astle |
| 6,686,149 B1 | 2/2004 | Sanchis et al. |
| 6,703,228 B1 | 3/2004 | Landers |
| 6,709,692 B2 | 3/2004 | Sudor |
| 6,743,640 B2 | 6/2004 | Whitten et al. |
| 6,995,256 B1 | 2/2006 | Li et al. |
| 7,014,113 B1 | 3/2006 | Powell et al. |
| 7,015,030 B1 | 3/2006 | Fouillet et al. |
| 7,031,927 B1 | 4/2006 | Beck et al. |
| 7,060,874 B2 | 6/2006 | Wilkins |
| 7,112,616 B2 | 9/2006 | Takizawa et al. |
| 7,115,301 B2 | 10/2006 | Sheu et al. |
| 7,133,726 B1 | 11/2006 | Atwood et al. |
| 7,160,996 B1 | 1/2007 | Cook |
| 7,223,906 B2 | 5/2007 | Davis |
| 7,250,195 B1 | 7/2007 | Storey et al. |
| 7,709,250 B2 | 5/2010 | Corbett et al. |
| 7,732,492 B2 | 6/2010 | Makino et al. |
| 8,278,807 B2 | 10/2012 | Agneray et al. |
| 8,597,549 B2 | 12/2013 | Cumpston et al. |
| 9,297,032 B2 | 3/2016 | Jung |
| 2001/0039018 A1 | 11/2001 | Matson et al. |
| 2002/0048822 A1 | 4/2002 | Rittenburg et al. |
| 2002/0051969 A1 * | 5/2002 | Goto ............... C07K 14/70578 435/6.11 |
| 2002/0056147 A1 | 5/2002 | Dau et al. |
| 2002/0064639 A1 * | 5/2002 | Rearick ................ A41D 31/00 428/292.1 |
| 2002/0080994 A1 | 6/2002 | Lofgren et al. |
| 2002/0119485 A1 | 8/2002 | Morgan |
| 2002/0128234 A1 | 9/2002 | Hubbell et al. |
| 2002/0137893 A1 | 9/2002 | Burton et al. |
| 2002/0155490 A1 | 10/2002 | Skinner et al. |
| 2002/0160360 A1 | 10/2002 | Chenchik et al. |
| 2002/0167161 A1 | 11/2002 | Butland |
| 2002/0129251 A1 | 12/2002 | Itakura |
| 2002/0185634 A1 | 12/2002 | Marder et al. |
| 2002/0187263 A1 | 12/2002 | Sheu et al. |
| 2003/0000225 A1 | 1/2003 | Nagai et al. |
| 2003/0017551 A1 | 1/2003 | Parthasarathy et al. |
| 2003/0035917 A1 | 2/2003 | Hyman |
| 2003/0064507 A1 | 4/2003 | Gallagher et al. |
| 2003/0096273 A1 | 5/2003 | Gagna |
| 2003/0142704 A1 | 7/2003 | Lawandy |
| 2003/0142713 A1 | 7/2003 | Lawandy |
| 2003/0162296 A1 | 8/2003 | Lawandy |
| 2003/0177095 A1 | 9/2003 | Zorab et al. |
| 2003/0203387 A1 | 10/2003 | Pelletier |
| 2003/0207331 A1 | 11/2003 | Wilson, Jr. et al. |
| 2004/0063117 A1 | 4/2004 | Rancien et al. |
| 2004/0071718 A1 | 4/2004 | Tsai |
| 2004/0115796 A1 | 6/2004 | Bums |
| 2004/0166520 A1 | 8/2004 | Connolly |
| 2004/0219287 A1 | 11/2004 | Regan et al. |
| 2005/0008762 A1 | 1/2005 | Sheu et al. |
| 2005/0031120 A1 | 2/2005 | Samid |
| 2005/0045063 A1 | 3/2005 | Niggemann et al. |
| 2005/0053968 A1 | 3/2005 | Bharadwaj et al. |
| 2005/0059029 A1 | 3/2005 | Mariella, Jr. et al. |
| 2005/0059059 A1 | 3/2005 | Liang |
| 2005/0112610 A1 * | 5/2005 | Lee ..................... C12Q 1/6876 435/6.13 |
| 2005/0142565 A1 | 6/2005 | Samper et al. |
| 2005/0214532 A1 * | 9/2005 | Kosak ............... C12Q 1/6813 428/364 |
| 2005/0260609 A1 | 11/2005 | Lapidus |
| 2006/0017957 A1 | 1/2006 | Degott et al. |
| 2006/0017959 A1 | 1/2006 | Downer et al. |
| 2006/0117465 A1 | 6/2006 | Willows et al. |
| 2006/0121181 A1 | 6/2006 | Sleat et al. |
| 2006/0199196 A1 | 9/2006 | O'Banion et al. |
| 2006/0286569 A1 | 12/2006 | Bar-Or et al. |
| 2007/0012784 A1 * | 1/2007 | Mercolino ........... G01N 21/643 235/491 |
| 2007/0026239 A1 | 2/2007 | Sigrist et al. |
| 2007/0048761 A1 | 3/2007 | Reep et al. |
| 2007/0072197 A1 | 3/2007 | Rayms-Keller et al. |
| 2007/0117119 A1 | 5/2007 | Akita et al. |
| 2007/0121937 A1 | 5/2007 | Kochevar et al. |
| 2007/0254292 A1 * | 11/2007 | Fukasawa ......... C12N 15/1006 435/6.12 |
| 2008/0038813 A1 | 2/2008 | Chen |
| 2008/0081357 A1 | 4/2008 | Kwon et al. |
| 2008/0149713 A1 | 6/2008 | Brundage |
| 2008/0153135 A1 | 6/2008 | Liu |
| 2008/0216255 A1 | 9/2008 | Poovey et al. |
| 2008/0290649 A1 | 11/2008 | Klein et al. |
| 2008/0293052 A1 | 11/2008 | Liang et al. |
| 2008/0299559 A1 | 12/2008 | Kwok et al. |
| 2008/0299667 A1 | 12/2008 | Kwok et al. |
| 2008/0312427 A1 | 12/2008 | Kwok et al. |
| 2009/0042191 A1 | 2/2009 | Hayward et al. |
| 2009/0057147 A1 | 3/2009 | Kayyem |
| 2009/0075261 A1 | 3/2009 | Hayward et al. |
| 2009/0136163 A1 | 5/2009 | Kerr et al. |
| 2009/0220789 A1 | 9/2009 | DeSimone et al. |
| 2009/0222912 A1 | 9/2009 | Boschin |
| 2009/0253127 A1 | 10/2009 | Gaudreau et al. |
| 2009/0286250 A1 * | 11/2009 | Hayward ............. C09D 7/1233 435/6.11 |
| 2009/0069199 A1 | 12/2009 | Brandenburg |
| 2009/0311555 A1 | 12/2009 | Badyal et al. |

(56) References Cited

U.S. PATENT DOCUMENTS

| | | |
|---|---|---|
| 2009/0313740 A1 | 12/2009 | Santos et al. |
| 2009/0325234 A1 | 12/2009 | Gregg et al. |
| 2010/0050344 A1 | 3/2010 | Peltz et al. |
| 2010/0065463 A1 | 3/2010 | Taylor |
| 2010/0075407 A1 | 3/2010 | Duffy et al. |
| 2010/0099080 A1 | 4/2010 | Church et al. |
| 2010/0149531 A1 | 6/2010 | Tang |
| 2010/0240101 A1 | 9/2010 | Lieberman et al. |
| 2010/0250616 A1 | 9/2010 | Kim |
| 2010/0258743 A1 | 10/2010 | Bortolin |
| 2010/0267091 A1 | 10/2010 | Murray et al. |
| 2010/0279282 A1 | 11/2010 | Liang et al. |
| 2010/0285447 A1 | 11/2010 | Walsh et al. |
| 2010/0285490 A1 | 11/2010 | Dees et al. |
| 2010/0285985 A1 | 11/2010 | Liang et al. |
| 2010/0307120 A1* | 12/2010 | Stover .................. A01D 46/08 56/28 |
| 2011/0054938 A1 | 3/2011 | Hood et al. |
| 2011/0165569 A1 | 7/2011 | Macula |
| 2011/0229881 A1 | 9/2011 | Oshima |
| 2011/0250594 A1 | 10/2011 | Liang et al. |
| 2011/0263688 A1 | 10/2011 | Barany et al. |
| 2012/0115154 A1 | 5/2012 | Hampikian |
| 2012/0264742 A1 | 10/2012 | Furuishi et al. |
| 2013/0040150 A1 | 2/2013 | Trexler et al. |
| 2013/0040381 A1 | 2/2013 | Gregg et al. |
| 2013/0046994 A1 | 2/2013 | Shaw |
| 2013/0048731 A1 | 2/2013 | Flickner et al. |
| 2013/0109596 A1 | 5/2013 | Peterson et al. |
| 2013/0149706 A1 | 6/2013 | Kwok et al. |
| 2013/0222559 A1 | 8/2013 | Lebaschi et al. |
| 2013/0274129 A1 | 10/2013 | Katzen et al. |
| 2014/0099643 A1 | 4/2014 | Jung et al. |
| 2014/0106357 A1 | 4/2014 | Berrada et al. |
| 2014/0224673 A1 | 8/2014 | Alocilja |
| 2014/0256881 A1 | 9/2014 | Berrada et al. |
| 2014/0272097 A1 | 9/2014 | Jung et al. |
| 2014/0295423 A1 | 10/2014 | Liang et al. |
| 2015/0018538 A1 | 1/2015 | Berrada et al. |
| 2015/0030545 A1 | 1/2015 | Grass et al. |
| 2015/0083797 A1 | 3/2015 | Tran et al. |
| 2015/0125949 A1 | 5/2015 | Liss |
| 2015/0133319 A1 | 5/2015 | Fu et al. |
| 2015/0141264 A1 | 5/2015 | Jung et al. |
| 2015/0304109 A1 | 10/2015 | Tran et al. |
| 2016/0076088 A1 | 3/2016 | Tran et al. |

FOREIGN PATENT DOCUMENTS

| | | |
|---|---|---|
| EP | 0840350 A2 | 5/1998 |
| EP | 1063286 A1 | 12/2000 |
| EP | 1231470 A1 | 8/2002 |
| EP | 1237327 A2 | 9/2002 |
| EP | 140333 A1 | 3/2004 |
| EP | 1847316 A1 | 10/2007 |
| EP | 2428925 A1 | 3/2012 |
| EP | 2444136 | 4/2012 |
| EP | 2444546 A1 | 4/2012 |
| GB | 2319337 A | 5/1998 |
| GB | 2434570 A1 | 8/2007 |
| JP | 63-503242 | 11/1988 |
| JP | 2009517250 A | 4/2009 |
| RU | 2084535 C | 7/1997 |
| RU | 2170084 C1 | 7/2001 |
| WO | 8706383 A1 | 10/1987 |
| WO | 90/144441 A1 | 11/1990 |
| WO | 9506249 A1 | 3/1994 |
| WO | 95/02702 A1 | 1/1995 |
| WO | 9502702 A1 | 1/1995 |
| WO | 95/06249 A1 | 3/1995 |
| WO | 9806084 A1 | 2/1996 |
| WO | 97/04392 A1 | 2/1997 |
| WO | 9745539 A1 | 12/1997 |
| WO | 98/16313 A1 | 4/1998 |
| WO | 99/45514 A1 | 9/1999 |
| WO | 9959011 A1 | 11/1999 |
| WO | 00/61799 A2 | 10/2000 |
| WO | 0125002 A1 | 4/2001 |
| WO | 2001036676 | 5/2001 |
| WO | 0055609 A1 | 9/2001 |
| WO | 0199063 A1 | 12/2001 |
| WO | 02057548 A1 | 7/2002 |
| WO | 02/066678 A2 | 8/2002 |
| WO | 02084617 A1 | 10/2002 |
| WO | 03/016558 A1 | 2/2003 |
| WO | 03030129 A2 | 4/2003 |
| WO | 03/038000 A1 | 5/2003 |
| WO | 30/080931 A1 | 10/2003 |
| WO | 2004025562 A1 | 3/2004 |
| WO | 2004/086323 A1 | 10/2004 |
| WO | 2005/075683 A1 | 8/2005 |
| WO | 2005/103226 A2 | 11/2005 |
| WO | 2006/109014 A1 | 10/2006 |
| WO | 2007078833 A | 7/2007 |
| WO | 2008/007060 A1 | 1/2008 |
| WO | 2008045288 A2 | 4/2008 |
| WO | 2008154931 A | 12/2008 |
| WO | 09/027806 A1 | 3/2009 |
| WO | 100075858 A1 | 3/2010 |
| WO | 2011/005222 A1 | 1/2011 |
| WO | 2012/076021 A1 | 6/2012 |
| WO | 2013/052924 A1 | 4/2013 |
| WO | 2013/154943 A1 | 10/2013 |
| WO | 2013170009 A1 | 11/2013 |
| WO | 2014/062754 A1 | 4/2014 |

OTHER PUBLICATIONS

M. Ageno, E Dore and C. Frontali The Alkaline Denaturation of DNA, Biophys. J. Nov. 1969, 9(11): 1281-1311.

T. Thiel, L. Liczkowski and S.T. Bissen New zwitterionic butanesulfonic acids that extend the alkaline range of four families of good buffers: Evaluation for use in biological Systems. J. Biochem. Biophys. Methods (1998) 37: 117-129. Elsevier.

Versalift, "Market Growth, the evolution of the aerial lift industry," Oct. 1, 2002. Accessed on web Nov. 10, 2008.

Schulz et al., "Archived or directly swabbed latent fingerprints as a DNA source for STR typing," Forensic Science International, 127 (2002) 128-130.

Zuckermann, et al. "Efficient methods for attachment of thiol specific probes to the 3' end of synthetic oligonucleotides." Nucleic Acids Research, vol. 15, pp. 5305-5321 (1987) IRL Press Limited, Oxford.

Whitcombe, et al. "Detection of PCR products using self-probing amplicons and fluorescence," Nature Biotechnology, vol. 17 pp. 804-807 (1999) Nature America, Inc. New York.

Tyagi, et al. Multicolor molecular beacons for allele discrimination, Nature Biotechnology, vol. 16, pp. 49-53 (1998) Nature Publishing Group, New York.

Nazarenko, et al. "A closed tube format for amplification and detection of DNA based on energy transfer," Nucleic Acids Research, vol. 25, pp. 2516-2521 (1997) Oxford University Press.

Tyagi & Kramer, "Molecular Beacons: Probes that Fluoresce upon Hybridization" nature Biotechnology, vol. 14, pp. 303-308 (1996) Nature Publishing Group, New York.

Sproat, et al. "The synthesis of protected 5'-mercapto-2',5'-didoexyribonucleoside-3-O-phosphoramidites, uses of 5'-mercapto-didoexyribonucleosides." Nucleic Acids Research, vol. 15, pp. 4837-4848 (1987) IRL Press Limited, Oxford.

Nelson, "Bifunctional oligonucleotide probes synthesized using a novel CPG support are able to detect single base pair mutations." Nucleic Acids Research, vol. 17, pp. 7187-7194 (1989) IRL Press Limited, Oxford.

Gupta, et al. "A general method for the synthesis of 3'-sulfhydryl and phosphate group containing oligonucleotides." Nucleic Acids Research, vol. 19, pp. 3019-3025 (1991) Oxford University Press, Oxford, England.

(56) References Cited

OTHER PUBLICATIONS

Lee, et al. "Allelic discrimination by nick translation PCR with fluorescent probes." Nucleic Acids Research, vol. 21, pp. 3761-3766 (1993) Oxford University Press, Oxford, England.
Holland, et al. "Detection of specific polymerase chain reaction product by utilizing the 5' [to] 3' exonuclease activity of Thermus aquaticus DNA polymerase." Proceedings of the National Academy of Sciences, USA vol. 86 pp. 1276-7280 (1991) National Academy of Sciences, Washington, DC.
Heid, et al. "Real Time Quantitative PCR." Genome Research, vol. 6, pp. 986-994 (1996) Cold Spring Harbor Laboratory Press, Woodbury, New York.
Gibson, et al. "A Novel Method for Real Time Quantitative RT-PCR" Genome Research, vol. 6, pp. 995-1001 (1996) Cold Spring Harbor Laboratory Press, Woodbury, New York.
Agrawal & Tang, "Site-specific functionalization of oligodoexynucleotides for non-radioactive labelling." Tetrahedron Letters, vol. 31, pp. 1543-1546 (1990) Pergamon Press, Great Britain.
Van Der Rijke, et al. " Up-converting phosphor reporters for nucleic acid microarrays." Nature Biotechnology, vol. 19, pp. 273-276 (2001) Nature Publishing Group, New York.
Corstjens, et al. "Infrared Up-converting phosphors for bioassays." IEE Proceedings-Nanobiotechnology, vol. 152, pp. 64-72 (2005) Institution of Engineering and Technology, London.
Hussein et al. "Molecular Characterization of Cotton Genotypes Using PCR-based Markers." Journal of Applied Sciences Research 3(10) 1156-1169 (2007). INSInet Publication.
Jiang, et al. "Polyploid formatioopn created unique avenues for response to selection in Gossypium (cotton)" Proceedings of the National Academy of Sciences, USA vol. 95 pp. 4419-4424 (1998) National Academy of Sciences, Washington, DC.
Lee, et al. "The complete genome sequence of Gossypium hursutum, organization and phylogenetic relationships to other angiosperms." BMC Genomics 7:61, Mar. 2006.
Ibrahim, et al. Complete nucleotide sequence of the cotton (*Gossypium barbadense* L.) chloroplast genome with a comparative analysis of sequence among 9 dicot plants. Genes and Genetic Systems vol. 81. pp. 311-321 (2006).
Kaneda, S. et al. Modification of the glass surface property in PDMS-glass hybrid microfluidoc devces. Analytical Sciences, Jan. 2012, vol. 28, No. 1, pp. 39-44.
Hosokawa, K. et al. DNA Detection on a power-free microchip with laminar flow-assisted dendritic amplification. Analytical Sciences, 2010, Vo. 26, No. 10, pp. 1052-1057.
Park, H. et al. Stress response of fibroblasts adherent to the surface of plasma-treated poly(lactic-co-glucolic acid) nanofiber matrices. Colloids surf B Biointerfaces, May 2010, 1; 77(1):90-95.
Tuzlakoglu K. et al. A new route to produce starch-based fiber mesh scaffolds by wet spinning and subsequent surface modification as a way to improve cell attachment and proliferation. J Biomed Mater Res A, Jan. 2010, 92(1):369-377.
Karahan et al., Fibers and Polymers, vol. 9, pp. 21-26 (2008).
Ullrich, T. et al. Competitive reporter monitored amplification (CMA)-quantification of molecular targets by real time monitoring of competitive reporter hybridization. PLoS One, 2012, vol. 7, No. 4 E35438. doi;10.1371/journal.pone.0035438, p. 1-13.
Instant Krazy Glue, product description, accessed website Feb. 24, 2012, 4 pages.
Kim, Jeong AH et al., "Fabrication and Characterization of a PDMS-Glass Hybrid Continuous-Flow PCR Chip", Biochemical Engineering Journal, 29, 91-97 (2006).
Curcio, Mario et al., "Continuous Segmented-Flow Poymerase Chain Reaction for High-Throughput Miniaturized DNA Amplification" Analytical Chemistry, vol. 75, No. 1, 1-7 (Jan. 1, 2003).
Kopp, Martin U. et al, "Chemical Amplification: Continuous-Flow PCR on a Chip", Science, vol. 280, 1046-1048 (1998).
Skirtach, Andre, G. et al, "The Role of Metal Nanoparticles in Remote Release of Encapsulated Materials", Nano Letters, vol. 5, No. 7, 1371-1377 (2005).
Fixe, F. et al., Thin Film Micro Arrays with Immobilized DNA for Hybridization Analysis, Mat. Res. Soc. Symp. Proc. vol. 723, Materials Research Society, O2.3.1-O2.3.6 (2002).
Hayward, Jim et al., "A Scaled, Integrative Implementation for DNA Marking of Integrated Circuits", Applied DNA Sciences, 1-25 (2013).
Ovsianikov, Aleksandr et al., "Two-Photon Polymerization Technique for Microfabrication of CAD-Designed 3D Scaffolds from Commercially Available Photosensitive Materials", Journal of Tissue Engineering and Regenerative Medicine, 1:443-449 (2007).
Khandjian, E.W., "Optimized Hybridization of DNA Blotted and Fixed to Nitrocellulose and Nylon Membranes" Biotechnology, vol. 5, 165-167 (1987).
Chrisey, Linda A et al., "Fabrication of Patterned DNA Surfaces", Nucleic Acids Research, vol. 24, No. 15, 3040-3047 (1996).
Wollenberger, Louis V. et al.,"Detection of DNA Using Upconverting Phosphor Reporter Probes", SPIE, vol. 2985, 100-111 (1997).
Takara Bio, "Takara Bio to Produce DNA Fragments for DNA Microarrays on Industrial Scale", http://www.evaluategroup.com/Universal/View.aspx?type_Story&id.
Obeid, Pierre J. et al., "Microfabricated Device for DNA and RNA Amplification by Continuous-Flow Polymerase Chain Reaction and Reverse Transcription-Polymerase Chain Reaction with Cycle Number Section", Anal. Chem, 75, 288-295 (2003).
Yang, XF, et al., "Fluorimetric determination of hemoglobin using spiro form rhodamine B hydrazide in a micellar medium", Talanta Nov. 12, 2003; 61(4): 439-45.
Hashimoto, Masahiko et al., "Rapid PCR in a Continuous Flow Device", Lab Chip, 4, 638-645 (2004).
Thibaudau, Franck, "Ultrafast Photothermal Release of DNA from Gold Nanoparticles", J. Phys. Chem. Lett. 3, 902-907 (2012).
Berger, S.A. et al., "Flow in Curved Pipes", Ann. Rev. Fluid Mech., 15:461-512 (1983).
WiseGeek, "How Many Species of Bacteria Are There", http://www.wisegeek.org/how-many-species-of-bacteria-are-there.htm.
Hunicke-Smith, Scott P., "PCR and Cycle Sequencing Reactions: A New Device and Engineering Model", Dissertation, Stanford University, pp. i-xiv and 1-200, May 1997.
Hou, Sen, et al., "Method to Improve DNA Condensation Efficiency by Alkali Treatment", Taylor & Francis, Nucleosides, Nucleotides and Nucleic Acids, 28:725-735, 2009.
Wikipedia, "List of sequenced bacterial genomes", http://en.wikipedia.org/wiki/List_of_sequenced_bacterial_genomes.
Wikipedia, "Virus", http://en.wikipedia.org/wiki/Virus.
Beija, Mariana, et al., "Synthesis and applications of Rhodamine derivatives as fluorescent probes", Chem. Soc. Rev., 2009, 38, 2410-2433.

* cited by examiner

METHOD AND DEVICE FOR MARKING ARTICLES

RELATED APPLICATIONS

This application claims the benefit of U.S. Provisional patent application Ser. No. 61/883,874, filed Sep. 27, 2013; and this application is a continuation in part of U.S. patent application Ser. No. 13/789,093, filed Mar. 7, 2013, the disclosures of which are incorporated by reference herein in their entireties.

TECHNICAL FIELD

The invention pertains to a method and device for marking articles, and more particularly to a method and device for marking articles with a nucleic acid marker to identify and authenticate the article's origin or authenticity.

BACKGROUND

Cotton is an essential cash crop throughout the world. Many parts of the cotton plant are useful; however, cotton is particularly important in forming a variety of goods, for example, fabrics, clothing and many household items such as towels and tablecloths, etc. The use of cotton to generate fabric initially requires the processing of bales of cotton to liberate cotton fibers. Bales of cotton are typically opened by automated machinery to remove unprocessed lint. The lint can then be further cleaned by, for example, using a blower to separate short components of the lint from cotton fibers. The cotton fibers can then be woven into longer strands sometimes referred to as cotton yarn. The woven cotton fibers are useful in the manufacture of many different items, for example, fabrics, clothing and household items. A single pound of cotton may yield many millions of cotton fibers. However, the lengths of individual cotton fibers vary according to the species or cultivars of the cotton plant from which the fibers originated.

The quality of fabrics produced from cotton fibers vary according to the length of the individual cotton fibers. Relatively short cotton fibers are commonly harvested, for example, from the cotton species *G. hirsutum, G. herbaceum,* and *G. arboreum*. The relatively short fibers are generally considered of lower quality than longer cotton fibers harvested from the cotton species *G. barbadense. G. barbadense*-derived cotton fibers are commonly referred to as Extra Long Staple (ELS) cotton. ELS cotton is generally considered to produce higher quality and higher value fabrics, clothing, household items, and related products. Types of ELS cotton include, for example, American Pima, Egyptian, and Indian Suvin. Products carrying an ELS label, such as the aforementioned, American Pima, Egyptian, Supima, or Indian Suvin labels will generally command a higher price than products lacking such a designation.

Variability in cotton quality has lead to concerns over the authenticity of and accurate identification of quality cotton products. Once raw cotton or products containing cotton enter into the stream of commerce, which may include worldwide trade, it is often difficult to reliably determine whether cotton advertised as ELS cotton is, in fact, authentic or is blended or is composed entirely of short fiber cotton. It also may be difficult to determine whether a particular cotton product originated from a particular location, region or manufacturer. For example, counterfeit products manufactured from short fiber cotton may be inappropriately or fraudulently labeled as ELS, American Pima, Egyptian, or Indian Suvin cotton. Cotton products may also be fraudulently labeled as originating from a particular region of the world (e.g., as Egyptian cotton). There is an unmet need for a method of determining whether a particular article of cotton is entirely composed of authentic ELS cotton, or is a counterfeit article that includes significant amounts of or is in fact entirely composed of short staple cotton.

Counterfeiting and blending of high-end products with cheaper material has become a major liability problem for major brand names. The International Chamber of Commerce (ICC) reported that in 2008, counterfeited goods resulted in a loss of $650 billion in revenues and 2.5 million jobs. The ICC projected that the loss in revenues will exceed $1.7 trillion in 2015, which is equivalent to 2% of the world economy. In addition to the revenue losses, certain counterfeit products were linked directly to serious health and safety issues. The counterfeit goods have infiltrated most industries from textiles to microchips, and even pharmaceuticals.

SUMMARY

Exemplary embodiments of the present invention provide a method for marking an article. The method includes depositing a solution comprising a nucleic acid marker onto at least a portion of the article. The deposition may be performed with a delivery mechanism comprising one or more outlets. The nucleic acid marker may be activated, for example, by adding a functional group to the nucleic acid marker.

In accordance with an exemplary embodiment of the invention, the nucleic acid marker may include DNA. In another exemplary embodiment, the DNA may be alkaline activated. In another exemplary embodiment, an amount of the solution comprising the nucleic acid marker deposited on the article may be regulated, such as for instance, by a metering control.

In another exemplary embodiment, the marked article may include a material, such as for instance, a textile, a fiber, cotton, ginned cotton, a cotton blend, wool, yarn, nylon, or cashmere. The marked article may include a synthetic fabric or a synthetic fabric blend including, for example, rayon, nylon, wool, or polyester. The polyester synthetic fiber may include homopolymers, copolymers, aliphatics and/or aromatics. The polyester synthetic fiber may include any suitable polyester, such as for instance, polyethylene, polypropylene, or polyethylene terephthalate to name a few, and may be blended with other fibers, such as cotton fibers. The article may include raw fibers. The solution comprising the nucleic acid marker may be deposited on the raw fibers during or after a scouring process is performed on the raw fibers.

In another exemplary embodiment, the marked article may include an electronics article, such as for instance, a computer, a computer component, a network component, a computer disk, a microchip, a microcircuit, a semiconductor, a diode, a transistor, an integrated circuit, an optoelectronic device, a digital display, a vacuum tube, a discharge device, a power source, a resistor, a capacitor, a battery, a magnetic device, a sensor, a detector, a transducer, an electronics assembly, a terminal, a cable, or a switch, to name but a few electronics components.

In another exemplary embodiment, the marked article may include a liquid, such as for instance, an ink, a solvent, an alcohol, or an adhesive.

In another exemplary embodiment, the marked article may include a commodity, such as for instance, iron ore, crude oil, gasoline, coal, or a metal, such as for instance, aluminum, copper, gold, silver, palladium, or platinum.

In another exemplary embodiment, the marked article may include a pharmaceutical packaging, such as for instance, a pharmaceutical packaging, a pharmaceutical label, a pharmaceutical packaging insert, or a pharmaceutical packaging cap.

Exemplary embodiments of the present invention provide a device for marking an article. The device includes a surface, such as a substrate, a platform or a transport mechanism adapted to transport an article in a direction of a delivery mechanism positioned at a location along the transport mechanism. The delivery mechanism includes one or more outlets. The delivery mechanism is adapted to deposit a solution comprising an activated nucleic acid marker through the one or more outlets onto at least a portion of the article.

BRIEF DESCRIPTION OF THE DRAWINGS

Embodiments for the following description are shown in the following drawings.

DETAILED DESCRIPTION

Figure 1:
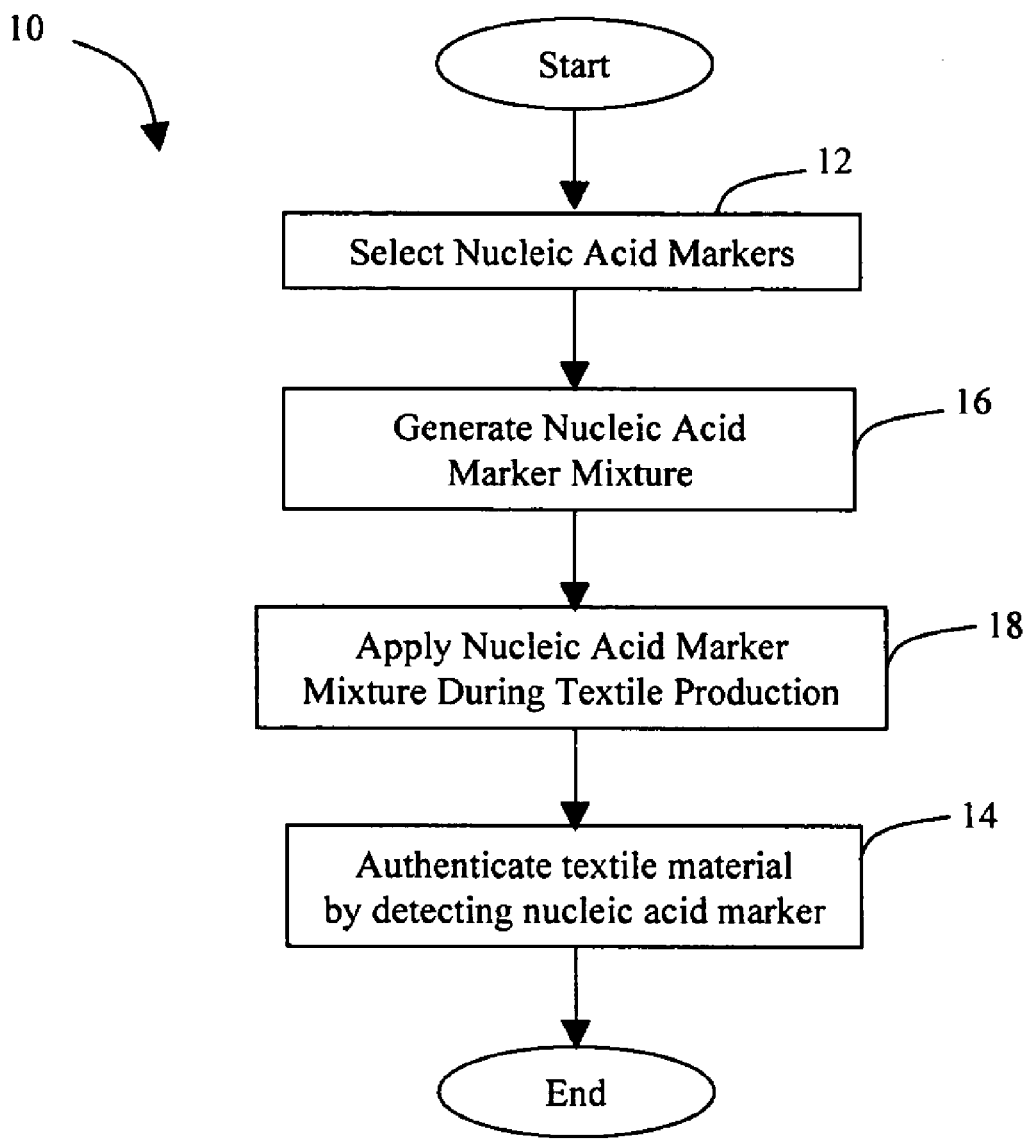
FIG. 1 is a flowchart of a method for authenticating a textile material.

Exemplary embodiments of the present invention will be described below in more detail with reference to the accompanying drawings. Exemplary embodiments of the invention may, however, be embodied in different forms and should not be construed as limited to the embodiments set forth herein.

Exemplary embodiments of the present invention provide a method for marking an article. The method includes depositing a solution comprising a nucleic acid marker onto at least a portion of the article. The deposition is performed with a delivery mechanism comprising one or more outlets. The nucleic acid marker may be activated, for example, by adding a reactive group to the nucleic acid marker.

Marker Molecules

In an exemplary embodiment of the present invention, a marker molecule to be deposited, linked, attached or bonded to the article may be a biomolecule (e.g., a nucleic acid marker). The marker molecule may be an inorganic molecule and may include one or more metals, non-metals or rare earth metals. The biomolecule may be a protein, a peptide, a nucleic acid, a vitamin, or a protein-DNA complex. The nucleic acid may comprise, for example, RNA, DNA, an RNA-DNA complex, single stranded DNA or double stranded DNA. The nucleic acid may be any suitable size, for example, the nucleic acid may be in a range of about 50 base pairs to about 1000 base pairs. The nucleic acid may comprise any suitable natural or non-natural DNA sequence such as a synthetic DNA sequence that is not a natural DNA sequence. The non-natural DNA sequence may be formed by digesting and religating naturally or non-naturally occurring DNA. The DNA may be from any source, such as for instance, animal or plant DNA. The DNA may be derived from bacteria, viruses, fungi, or synthetic vectors or fragments or any combination thereof. The nucleic acid may comprise a non-naturally occurring DNA sequence formed by, for example, digesting and religating animal or plant DNA. The nucleic acid may include synthetic DNA, semi-synthetic DNA of a combination of synthetic and semi-synthetic DNA. The nucleic acid may comprise nuclear, mitochondrial or chloroplast DNA or total genomic DNA.

In an exemplary embodiment of the present invention, the nucleic acid marker may be derived from any suitable DNA source, such as for instance, DNA extracted from a plant source. The nucleic acid marker including DNA may interchangeably be referred to as a DNA taggant. The extracted DNA may be specifically or randomly digested and ligated to generate artificial nucleic acid sequences which are unique to the world. The digestion and ligation of the extracted DNA may be completed by standard restriction digestion and ligation techniques known to those skilled in the art of molecular biology. Digestion may be performed randomly or site-specifically, for example by random or site specific nucleases. The nucleic acid fragments resulting from digestions may be specifically or randomly rearranged to form new nucleic acid sequences (e.g., non-natural nucleic acid sequences). The sequence of the nucleic acid marker can be of any suitable length, for instance the sequence of the nucleic acid marker can be a sequence of from about 5 to about 5000 bases or a sequence from about 20 to about 1000 bases.

In an exemplary embodiment of the invention, the nucleic acid marker may include activated DNA, or any suitable functionalized DNA, for example, an alkaline pH activated DNA (see below). The method may include depositing the nucleic acid marker onto the surface of the article or into a liquid for binding, linking or attaching of the activated nucleic acid marker to the article, for example, onto a surface of the article or a portion of the surface of the article. The nucleic acid marker may be incorporated into the material or a portion of the material from which the article is formed. The alkaline pH activated nucleic acid marker including alkaline activated DNA may be bound to a material, such as, for instance, cotton, wool, nylon, plastic, metal, glass, wood, or printing ink. Alkaline activation of a nucleic acid marker is discussed in more detail below.

FIG. 1 is a flowchart of a method for authenticating a textile material. Referring to FIG. 1, a method 10 for authenticating an article, such as a textile material is shown. The method is initiated at block 12 by selecting the nucleic acid marker. The term nucleic acid, which may be abbreviated as "NA" in the Figures, may refer to deoxyribonucleic acid (DNA) or ribonucleic acid (RNA). Nucleic acid markers may include nucleic acids from animals, plants, bacteria, viruses, fungi, or synthetic vectors or fragments or any combination thereof. The nucleic acid marker may be any suitable nucleic acid, such as for instance, a synthetic non-natural DNA, a semi-synthetic DNA derived from natural and synthetic sequences or a rearranged natural DNA sequence derived by cleavage and ligation of the cleavage fragments in a new non-natural sequence.

The nucleic acid marker may have a specific template sequence and/or a specific template length, so that when polymerase chain reaction (PCR) procedures are performed, PCR primers may be any specific primer pairs with a complementary nucleic acid sequence which can bind nucleic acids of the nucleic acid marker template. There may be a relatively low concentration of nucleic acids in the nucleic acid marker and the nucleic acids may be amplified by techniques well known to those skilled in the art of molecular biology.

The nucleic acid marker may be mixed into solution with water or any desired aqueous solution or buffer to form the solution comprising the nucleic acid marker for use in the methods of the invention. For example, nucleic acids may be mixed with water to form the solution comprising the nucleic acid marker. The solution comprising the nucleic acid marker may be mixed at any desired concentration to mark the article. For example, the concentration of nucleic acid to solvent may be approximately 1 attogram/milliliter ($10^{-18}$ g/m), 1 femptogram/milliliter ($10^{-15}$ g/ml), 1 picogram/milliliter ($10^{-12}$ g/m), 1 nanogram/milliliter ($10^{-9}$ g/ml) or 1 microgram/milliliter ($10^{-6}$ g/m). Alternatively, the concentration of nucleic acid in the solution may be in a range from approximately 1 attogram/milliliter ($10^{-18}$ g/m) to approximately 1 microgram/milliliter ($10^{-6}$ g/m). The solution comprising the nucleic acid marker may include more than one nucleic acid marker.

It will also be appreciated by those of skill in the art that the nucleic acid marker may be combined with one or more optical reporters, for instance, an infrared marker. For example, the optical reporter may be chemically linked to the nucleic acid marker or the optical reporter may be mixed into the solution comprising the nucleic acid marker. The optical reporter may be, for instance, an upconverting phosphor or a fluorophore. The nucleic acid marker and the optical reporter can be mixed in a dyeing process. The combination or mixture of the nucleic acid marker and the optical reporter may be applied to one or more articles, such as for instance, fibers or fibrous materials. The fibers or fibrous materials may be materials suitable for being combined to form textiles. The marked fibers may then be blended with one or more unmarked fibers to generate a marked textile. The blending of the marked fibers with the unmarked fibers may be performed during ginning, before opening, during opening, before blending, or during blending. The fibers may be raw fibers, and may be marked during or after scouring. Raw fibers (e.g., raw cotton fibers or raw wool fibers) may refer to fibers that have been ginned, or ginned and scoured. For example, the raw fibers that have been separated from cotton plant material by ginning, but that have not yet been scoured may include small plant parts and foreign matter that is not removed by the ginning process.

Activation of Nucleic Acids

Nucleic acids (e.g., DNA) can be activated to enhance binding between the nucleic acid and an article to be marked by methods well known in the art (See for instance, G. T. Hermanson, *Bioconjugate Techniques*, 2d ed., 2008, Academic Press). Activating the nucleic acid may make the nucleic acid physically or chemically reactive with the surface of the article to be marked (e.g., by rendering the nucleic acid capable of ionically or covalently bonding to an available group on the surface of the article). For example, the nucleic acid may be activated by exposure to alkaline conditions. Alkaline activation of nucleic acids is discussed in more detail below.

A reactive functional group may be bound to the nucleic acid to facilitate binding between the nucleic acid and the article to be marked. The reactive functional group may be bound to the nucleic acid through a process of alkaline activation of the DNA molecule (described in more detail below). The reactive functional group may be capable of covalently binding to an available group on at least a portion of the article to be marked. The reactive functional group may immobilize the nucleic acid to the article.

The nucleic acid may be bound to at least a portion of the surface of the article by a chemical linker bound to a reactive functional group. For example, the chemical linker may include a chain of carbon atoms with a reactive functional group at an end of the chain of carbon atoms. The end of the chain of carbon atoms opposite to the reacting functional group may be covalently bound to the nucleic acid. The reactive functional group may be activated to covalently bind with an available group on the surface of the article. Activation of the reactive functional group may be performed by exposure to alkaline conditions. Alkaline activation is discussed in more detail below. The solution comprising the nucleic acid marker may include an activated nucleic acid as described herein.

Alkaline Activation of Nucleic Acids

The hydroxide anion has the chemical formula: OH⁻. It consists of an oxygen atom and a hydrogen atom held together by a covalent bond, and carries a negative electric charge. It is an important constituent of water. It functions as a base, as a ligand, a nucleophile, and a catalyst. The hydroxide ion forms salts, some of which dissociate in aqueous solution, liberating solvated hydroxide ions.

In organic chemistry, the hydroxide ion can act as a catalyst or as a nucleophilic reagent. An hydroxyl (OH) group, is present in alcohols, phenols, carboxylic acids and related functional groups.

Water is at equilibrium with its component ions:

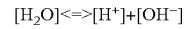

Water contains a concentration of $10^{-7}$ M [H⁺] ions. This is expressed as water having a pH of 7.0 on the logarithmic scale.

Strong alkalis are almost completely dissociated. Thus, the strong alkali, sodium hydroxide is essentially completely dissociated in an aqueous solution.

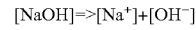

Water is only partly dissociated and has a fixed dissociation constant K according to the formula:

$$K = \frac{[H^+] \times [OH^-]}{[H_2O]}$$

Thus, an increase in the concentration of the OH⁻ ion forces the lowering of the concentration of H⁺ ions, by covalent binding to produce water molecules. Using this formula the concentration of [H⁺] and thus the pH of a sodium hydroxide solution can be readily estimated:

1.0 M NaOH contains $10^{-14}$ M [H⁺] ions, i.e. has a pH of 14.0;
0.1 M NaOH contains $10^{-13}$ M [H⁺] ions, i.e. has a pH of 13.0;
0.01 M NaOH contains $10^{-12}$ M [H⁺] ions, i.e. has a pH of 12.0;
0.001 M NaOH contains $10^{-11}$ M [H⁺] ions, i.e. has a pH of 11.0;
0.0001 M NaOH contains $10^{-10}$ M [H⁺] ions, i.e. has a pH of 10.0;
0.00001 M NaOH contains $10^{-9}$ M [H⁺] ions, i.e. has a pH of 9.0; and so on.

Alkaline extraction of DNA from cells of organisms takes advantage of the alkali-stable nature of DNA. Cell membranes are disrupted by treatment with alkali, releasing the cellular contents, and melting the double-stranded the total genomic DNA, including nuclear and mitochondrial DNA as the single stranded DNA forms. These DNA strands readily re-hybridize, snapping back to their original double stranded helical structure that can be isolated from the alkali-treated cellular millieu.

Alkali treatment of DNA may activate the DNA for covalent binding. Alkaline conditions may lead to ionization of the free hydroxyls at the 3' ends of the DNA strands. The negatively charged —O⁻ group produced at the 3' end of the DNA is a strong nucleophile, reactive with positively charged groups to form stable covalent bonds, stably binding the DNA.

The invention provides methods of binding of a nucleic acid (e.g., DNA) to an article. The method may include exposing the nucleic acid to alkaline conditions, and contacting the nucleic acid to the article. The nucleic acid bound to the article may be available for binding by hybridization probes, PCR amplification and DNA sequencing methods.

In one embodiment, the alkaline conditions are produced by mixing the DNA with an alkaline solution having a high pH, for instance the pH of the alkaline solution can be a pH of about 9.0 or higher; a pH of about 10.0 or higher; a pH of about 11.0 or higher, or even a pH of about 12.0 or higher, and contacting the DNA that has been exposed to the alkaline conditions with the substrate. In one embodiment, the alkaline solution is a solution of a hydroxide of an alkali metal.

An exemplary embodiment of the present invention provides a method of binding a nucleic acid marker (e.g., a nucleic acid marker including deoxyribonucleic acid) to the article, the method including exposing the DNA to alkaline conditions, wherein the alkaline conditions are produced by mixing the DNA with an alkaline solution, and contacting the DNA that has been exposed to the alkaline conditions with the article; wherein the alkaline solution is a solution of a hydroxide of an alkali metal and the alkali metal is selected from the group consisting of lithium (Li), sodium (Na), rubidium (Rb), and cesium (Cs).

An exemplary embodiment of the invention provides a method of binding the nucleic acid marker (e.g., a nucleic acid marker including DNA) to the article, the method including exposing the DNA to alkaline conditions, wherein the alkaline conditions are produced by mixing the DNA with an alkaline solution, and contacting the DNA that has been exposed to the alkaline conditions with the article; wherein the alkaline solution is a solution of an alkali metal hydroxide, wherein the alkali metal hydroxide is selected from the group consisting of lithium hydroxide (LiOH), sodium hydroxide (NaOH) and cesium hydroxide (CsOH). In one embodiment, the alkali metal hydroxide is sodium hydroxide (NaOH).

An exemplary embodiment the invention provides a method of binding the nucleic acid marker (e.g., a nucleic acid marker including DNA) to the article, the method including exposing the DNA to alkaline conditions, and contacting the DNA that has been exposed to the alkaline conditions with the article; wherein the alkaline conditions are produced by mixing the DNA with a solution of an alkali metal hydroxide, wherein the alkali metal hydroxide solution having a concentration of from about 1 mM to about 1.0 M. In another embodiment the alkaline conditions are produced by mixing the DNA with a solution of an alkali metal hydroxide, the alkali metal hydroxide solution having a concentration of from about 10 mM to about 0.9 M. In still another embodiment the alkaline conditions are produced by mixing the DNA with a solution of an alkali metal hydroxide, the alkali metal hydroxide solution having a concentration of from about 0.1 M to about 0.8 M. In yet another embodiment the alkaline conditions are produced by mixing the DNA with a solution of an alkali metal hydroxide, the alkali metal hydroxide solution having a concentration of from about 0.4 M to about 0.8 M. In still another exemplary embodiment the alkaline conditions are produced by mixing the DNA with a solution of an alkali metal hydroxide, the alkali metal hydroxide solution of about 0.6 M.

An exemplary embodiment of the invention provides a method of binding of the nucleic acid marker (e.g., a nucleic acid marker including DNA) to the article, wherein the method includes exposing the DNA to alkaline conditions and contacting the alkaline exposed DNA to the article, wherein the DNA is mixed with an alkaline solution having a pH from about 9.0 to about 14.0 and incubated at a temperature of from about 0° C. to about 65° C. to produce the alkaline conditions. Alternatively, the incubation temperature may be from about 5° C. to about 55° C., or from about 10° C. to about 45° C., or from about 15° C. to about 35° C., or from about 15 C to about 22° C. to produce the alkaline conditions. In another exemplary embodiment the alkaline conditions are produced by mixing the DNA with an alkali metal hydroxide solution having concentration of from about 0.1 M to about 1.0 M and incubating the mixture for a period of from about 1 minute to about 6 hours at a temperature of from about 10° C. to about 45 C, or from about 15° C. to about 25° C. to produce the alkaline conditions. In another exemplary embodiment the alkaline conditions are produced by mixing the DNA with an alkali metal hydroxide solution having concentration of about 0.6 M and incubating the mixture for a period of from about 1 minute to about 6 hours at a temperature of from about 15° C. to about 35° C., or from about 18° C. to about 22° C. to produce the alkaline conditions.

An exemplary embodiment of the invention provides a method of binding a nucleic acid marker (e.g., a nucleic acid marker including DNA) to an article, the method includes exposing the DNA to alkaline conditions, wherein the alkaline conditions are produced by mixing the DNA with an alkaline solution having a high pH, incubating the mixture and then neutralizing the alkaline solution and contacting the neutralized solution containing the DNA that has been exposed to the alkaline conditions with the article. In an exemplary embodiment, the alkaline solution is a solution of a hydroxide of an alkali metal selected from the group consisting of lithium (Li), sodium (Na), rubidium (Rb), and cesium (Cs).

An exemplary embodiment of the invention provides a method of binding a nucleic acid marker (e.g., a nucleic acid marker including DNA) to an article, the method includes exposing the DNA to alkaline conditions, and contacting the DNA that has been exposed to the alkaline conditions with the article; wherein the alkaline conditions are produced by mixing the DNA with an alkali metal hydroxide solution, and adding a molar excess of a polyionic polymer. The polyionic polymer can be any suitable polyionic polymer. In an exemplary embodiment of the present invention, the polyanionic polymer is a polyamino acid. The polyamino acid can be a homopolymer of a natural amino acid such as L-lysine, or a homopolymer of a non-naturally occurring amino acid, such as for instance D-lysine. In an exemplary embodiment, the polyamino acid homopolymer is selected from the group consisting of polyputrescine, polycadaverine, polyspermidine, and polylysine.

According to an exemplary embodiment of the invention, the nucleic acid marker (e.g., a nucleic acid marker including DNA) can be mixed with a solution of any suitable high pH buffer to produce the alkaline conditions. The high pH buffer can be any suitable high pH buffer with a pKa in a range of from about 9.0 to about 11.0 or higher. In an exemplary embodiment, the pH of the high pH buffer can be, for example, a pH of about 9.0 or higher; a pH of about 10.0 or higher; or a pH of about 11.0 or higher. For example, in an exemplary embodiment, DNA can be mixed with a suitable high pH buffer such as CABS (4-[cyclohexylamino]-1-butanesulphonic acid) with a useful pH range of about 10.0-11.4 (at 25° C.) and a pKa of about 10.70 (at 25° C.), Product No. C5580—Sigma Aldrich, St. Louis, Mo.; CAPS (N-cyclohexyl-3-aminopropanesulfonic acid) with a useful pH range of about 9.7-11.1 (at 25° C.), a pKa of about 10.56 (at 20° C.), a pKa of about 10.40 (at 25° C.) and a pKa of about 10.02 (at 37° C.), Sigma Aldrich Product Nos. C6070 and C2632; AMP (2-amino-2-methyl-1-propanol) with a useful pH range of about 9.0-10.5 (at 25° C.), a pKa of about 9.70 (at 25° C.), Sigma Aldrich Product Nos. A9199 and A9879; CAPSO (N-cyclohexyl-2-hydroxyl-3-aminopropanesulfonic acid) with a useful pH range of about 8.9-10.3 (at 25° C.), a pKa of about 9.60 (at 25° C.), a pKa of about 9.43 (at 37° C.), Sigma Aldrich Product Nos. C2278 and C8085; CHES (2-(N-cyclohexylamino) ethanesulphonic acid) with a useful pH range of about 8.60-10.0 (at 25° C.), a pKa of about 9.55 (at 20° C.), a pKa of about 9.49 (at 25° C.) and a pKa of about 9.36 (at 37° C.), Sigma Aldrich Product Nos. C2885 and C8210; AMPSO (3-[(1,1-dimethyl-2-hydroxyethyl)amino]-2-hydroxypropanesulfonic acid) with a useful pH range of about 8.3-9.7 (at 25° C.), a pKa of about 9.00 (at 25° C.), a pKa of about 9.10 (at 37° C.), Sigma Aldrich Product Nos. A6659 and A7585, to produce the alkaline conditions.

Generating a Solution Comprising a Nucleic Acid Marker for Textile Applications

The solution comprising the nucleic acid marker may be formed by mixing the nucleic acid in water. A concentrated solution of nucleic acid marker may be mixed with water to form the solution comprising the nucleic acid marker before the solution comprising the nucleic acid marker is deposited onto the article. The nucleic acid marker may be alkaline activated. For example, the nucleic acid marker may be exposed to the alkaline conditions discussed in detail above. An alkaline activator may be provided and the alkaline activator may be mixed with the solution comprising the nucleic acid marker to form an activated nucleic acid marker. The solution comprising the nucleic acid marker may be an aqueous solution comprising the nucleic acid marker. The solution comprising the nucleic acid marker may comprise any suitable working solution, such as an aqueous solution, which may include a buffer.

In an exemplary embodiment of the present invention, the solution comprising the nucleic acid marker may comprise a non aqueous solvent (e.g., polyurethane or silicone). The solution comprising the nucleic acid marker and the working solution may be mixed to form the solution comprising the nucleic acid marker according to the methods described in U.S. Pat. No. 7,115,301.

FIG. 1 is a flowchart of a method for authenticating a textile material. With reference to FIG. 1, at block 16 the solution comprising the nucleic acid marker may be generated by mixing the nucleic acid marker with a media that causes the nucleic acid marker to adhere to a fibrous material. For example, the nucleic acid marker may be mixed with water. The solution comprising the nucleic acid marker is then applied to the article, for example, a textile material such as a fiber or a fibrous material. As a result of this application, a marked fibrous material may be generated by causing the nucleic acid marker to adhere to the fibrous material. By way of example and not of limitation, the media may include an aqueous solvent, an adhesive, a polymer, a binder, or a cross-linking agent. The media may include an acrylic, polyurethane, dimethoyldihydroxyethyleneurea, polyvinyl alcohol, a starch, an epoxy, or polyvinyl chloride.

According to an exemplary embodiment of the invention, a media may be selected that is used as a topical treatment for a fibrous material. The media may be mixed with the nucleic acid marker to generate the solution comprising the nucleic acid marker suitable for topical treatment of the article. The solution comprising the nucleic acid marker may then be topically applied to the article (e.g., a fibrous material). The marked fibrous material may be generated by causing the nucleic acid marker to adhere to the fibrous material. The media suitable for topical treatment may include colorants, dyes, dyeing auxiliaries, print pastes, softeners, lubricants, antistatic agents, water repellants, antimicrobial agents, wetting agents, leveling agents, or water.

According to an exemplary embodiment of the invention, the media may be a viscous spinning solution for fiber spinning. The viscous spinning solution may be mixed with the nucleic acid marker to generate a viscous dope including the nucleic acid marker. The viscous dope may then be extruded through an opening in a spinneret to form the marked fiber. The marked fiber may then be solidified and can then be used in the textile manufacturing process. According to this exemplary method the solution comprising the nucleic acid marker may be embedded in the fiber.

According to an exemplary embodiment of the invention, the nucleic acid may be mixed with a water insoluble media to generate the solution comprising the nucleic acid marker. Firstly, the nucleic acid may be dissolved in a water soluble solution. The method then proceeds to dissolve the water insoluble media in a solvent. An intermediate solution is then used to mix the water soluble solution having the nucleic acid marker with the water insoluble media. The resulting solution comprising the nucleic acid marker is then applied to the desired article. By way of example and not of limitation, the intermediate solution used to generate the solution comprising the nucleic acid marker may include an organic solvent such as ethanol, acetone, chloroform or other such organic mixtures.

Referring to FIG. 1, at block 18 the solution comprising the nucleic acid marker may be deposited onto a textile article during a textile manufacturing process. There are a number of insertion points in the textile manufacturing process that can be used for depositing the solution comprising the nucleic acid marker onto a textile material. For example, the solution comprising the nucleic acid marker may be applied to a textile material during or after a scouring or ginning process (discussed below in more detail with reference to FIG. 5). A plurality of insertion points in the textile manufacturing process are described in further detail below.

Application of the Nucleic Acid Marker to an Article

In exemplary embodiments of the invention, the article may include a textile, a fiber, cotton, raw cotton, ginned cotton, a cotton blend, wool, yarn, cashmere, a synthetic fabric and a synthetic fabric blend. The article may be, for example, any natural material, fabric or raw material capable of being treated with the solution comprising the nucleic acid marker. The solution comprising the nucleic acid marker may be applied to fibers, yarns, sewing thread, fabrics, non-woven materials, and any product made from fibrous materials, such as a textile including wool or cotton fibers. The article may be any consumer product capable of being treated with the solution comprising the nucleic acid marker.

In an exemplary embodiment, the solution comprising the nucleic acid marker may be dried onto the article or absorbed into a material used to make the article. For example, the article may be a textile article including cotton or wool and the solution comprising the nucleic acid marker may be dried on the textile article. The solution comprising the nucleic acid marker may be dried by any suitable drying process, for example, air drying, oven drying, IR drying, or UV curing. Fibers may be any substance, natural or manufactured, with a high length-to-width ratio and with suitable characteristics for being processed into fabric in which the smallest component is hairlike in nature and can be separated from a fabric. Natural fibers may be those that are in a fiber form as they grow or develop and may be from animal, plant, or mineral sources, for example. Manufactured fibers (e.g., synthetic fibers) may be made from chemical compounds produced in manufacturing facilities. The manufactured fiber may be, for instance, Rayon or nylon.

Yarns may be an assemblage of fibers that are twisted or laid together so as to form a continuous strand that can be made into textile fabric or a textile article. A yarn may be a continuous strand of textile fibers, filaments, or materials in a form suitable for knitting, weaving, or otherwise intertwining to form a textile fabric. Filament yarns may be made from manufactured fibers, except for a relatively small percentage that is filament silk. Manufactured filament yarns may be made by extruding a polymer solution through a spinneret, solidifying it in fiber form, and then bringing the individual filaments together with or without a twist. Spun yarns may be continuous strands of staple fibers held together by a mechanism such as a mechanical twist that uses fiber irregularities and natural cohesiveness to bind the fibers together into one yarn.

Sewing thread may be a yarn intended for stitching materials together using machine or hand processes. Fabric may be a flexible planar material constructed from solutions, fibers, yarns, or fabrics, in any combination. A fabric may be a pliable, flat structure that can be made into two- or three-dimensional products that require some shaping and flexibility. Fabrics can be made from a wide variety of starting materials, such as for instance, solutions, fibers, yarns, "composite" fabrics, fiberglass or carbon fiber. For fabrics made from yarns, the fabric may be a woven or knitted fabric. Woven fabrics may be made with two or more sets of yarns interlaced at right angles. Knitting is a process which may form a fabric by the interlooping of one or more sets of yarns. Fabrics from solutions may include films in which the films are made directly from a polymer solution by melt extrusion or by casting the solution onto a hot drum. Composite fabrics are fabrics that combine several primary and/or secondary structures, at least one of which may be a recognized textile structure, into a single structure. Some fabrics may be made directly from fibers or fiber forming solutions without processing of fibers into a yarn. These nonwoven structures may include textile-sheet structures made from fibrous webs, bonded by mechanical entanglement of the fibers or by the use of added resins, thermal fusion, or formation of chemical complexes.

Those skilled in the art shall appreciate that the systems and methods described above may be used to mark articles, such as for instance, packaging materials, labeling materials, documents, and shipping containers for determining the origin, authenticity, or other supply chain or product information. In another exemplary embodiment, the marked article may include a pharmaceutical packaging, such as for instance, a pharmaceutical packaging, a pharmaceutical label, a pharmaceutical packaging insert, a pharmaceutical packaging cap or even on the pharmaceutical itself.

In exemplary embodiments of the invention, an article marked by a process is provided. The process may include providing the article and placing the article on any suitable surface for holding the article for deposition of the solution comprising the nucleic acid marker. For example, the article may be placed on a substrate, a surface, such as a platform, which may be a moving platform, or a conveyor belt. The method of marking the article may include conveying the article along the conveyor belt in the direction of the delivery mechanism positioned at a location along the conveyor belt. The delivery mechanism may comprise one or more outlets. The method of marking the article may include depositing the solution comprising the nucleic acid marker onto the article through the one or more outlets of the delivery mechanism and thereby marking the article. Exemplary apparatuses for marking the article are described below in more detail with reference to FIGS. 6 and 7.

Figure 2:
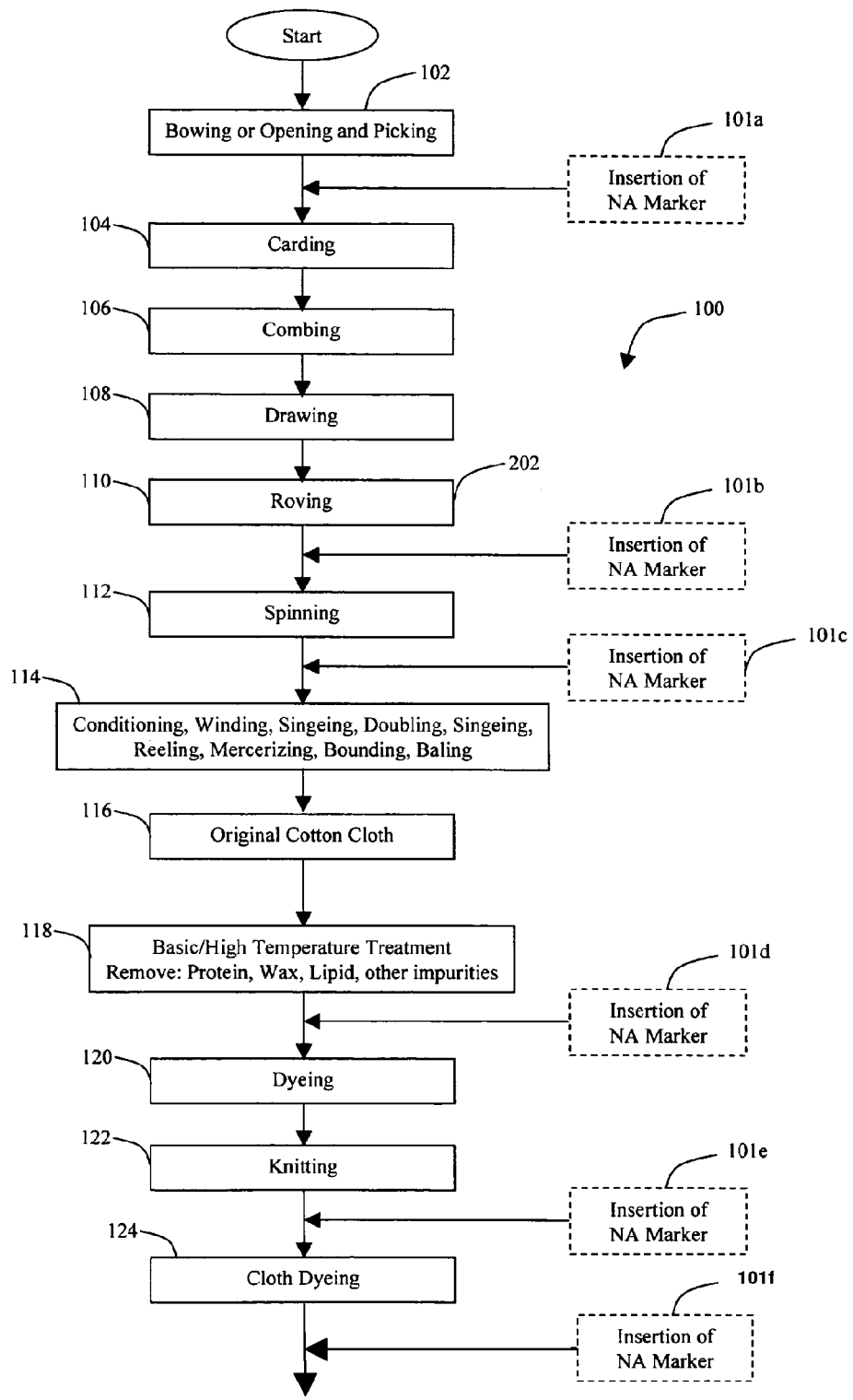
FIG. 2 is a flowchart of an illustrative textile manufacturing process having a variety of insertion points for the nucleic acid marker.

FIG. 2 is a flowchart of an illustrative textile manufacturing process having a variety of insertion points for the nucleic acid marker. The nucleic acid marker may be applied to a textile at any point during the manufacturing process for a textile (e.g., to a raw textile material such as raw wool or raw cotton), or to a textile at any point in the stream of commerce (e.g., a finished textile article passing through the stream of commerce). Referring to FIG. 2 an exemplary textile manufacturing process 100 is illustrated having a variety of insertion points for the nucleic acid marker. The nucleic acid marker may be applied as the solution comprising the nucleic acid marker as described above. The illustrative insertion points 101*a*, 101*b*, 101*c*, 101*d*, 101*e* and 101*f* for the solution comprising the nucleic acid marker provide for the application of the solution comprising the nucleic acid marker during the illustrative textile manufacturing process. During the textile manufacturing process, one or more solutions comprising the nucleic acid marker may be inserted at one or more insertion points of the manufacturing process. A database may be maintained to store information regarding each of the nucleic acid sequences for each manufacturer or process using the textile manufacturing process.

The first insertion point 101a may occur after the bowling or opening and picking process 102. The illustrative method then proceeds to the process steps of carding 104 during which staple fibers are drawn together in a somewhat parallel arrangement to form a relatively weak rope of fibers. The method continues to combing 106 which is an additional step in the production of smooth, fine, uniform spun yarns made of long-staple fibers. The next step is drawing 108 in which a manufactured fiber may be elongated after spinning to alter the molecular arrangement within the fiber. During roving 110, the elongated fiber may be reduced in size, fibers may be made more parallel, and a relatively small amount of twisting may be introduced.

The second illustrative insertion point 101b for the solution comprising the nucleic acid marker takes place after the roving 110 process and before spinning 112. Spinning 112 may refer to a process of producing yarn from raw or staple fibers. Spinning 112 may also refers to the production of a fiber by extruding a solution through small holes in a spinneret.

The third illustrative insertion point 101c occurs after spinning 112 and before block 116. In block 116, the illustrative following steps may be performed to form an original cotton cloth. Forming the original cotton cloth may include the steps of conditioning, winding, singeing, doubling, singeing, reeling, mercerizing, bounding and/or baling. Winding refers to a process of transferring yarn from one package to another. Singeing refers to a process of burning fiber ends to produce a smooth surface. Reeling refers to a process of removing fibers and winding the removed fibers into a reel. Mercerization refers to a finishing process in which sodium hydroxide is used to increase cotton's absorbency, luster and/or strength. After the original cotton cloth is generated 116, the method proceeds to block 118 in which a basic/high temperature treatment may be performed to remove, proteins, wax, lipids and other impurities.

The illustrative fourth insertion point 101d occurs after the high temperature treatment and before dyeing 120. The dyeing process block 120 may refer to the addition of color to the illustrative textile manufacturing process. Textiles may be produced by the use of dye or pigment mixtures. Pigments may include insoluble color particles that may be held on the surface of fabric by a binding agent. Dye may be an organic compound composed of a colored portion and may include a site that permits bonding to the fiber. Thus, for the illustrative fourth insertion point 101d the nucleic acid marker may be combined with a dye mixture or pigment mixture prior to attachment of the nucleic acid market to the textile.

After dyeing 120, the method proceeds to knitting 122. Knitting may refer to the process of fabric production by interlooping yarns. The illustrative fifth insertion point 101e occurs after knitting 122 and before cloth dyeing 124. The illustrative sixth insertion point 101f occurs after cloth dyeing 124. In the illustrative textile manufacturing process 100, the cloth dyeing process 124 may be performed after knitting 122 so that the knitted textile may be colored again. The nucleic acid marker may be combined with a dye mixture or pigment mixture prior to deposition on the textile. During the first three insertion points, namely 101a, 101b, 101c, the solution comprising the nucleic acid marker may be deposited directly onto a fiber or a fibrous material. As described above, the nucleic acid marker may be combined with a media that generates the solution comprising the nucleic acid marker that will cause the nucleic marker to adhere to the fibrous material or to products made from fibrous materials. The media may cause the nucleic acid marker to adhere to the fibrous material or to products made from fibrous materials. For example, the media may include an alkaline activator.

With respect to the fourth and fifth insertion points 101d, 101e and 101f, the nucleic acid marker may be deposited during "finishing" processes. A finishing process may be a process used to add color and augment performance of unfinished fabric. A finish may be a process that is performed, for example, on fiber, yarn, or fabric either before or after fabrication to change the appearance, the texture or feel, or the performance of the article.

The method for generating the solution comprising the nucleic acid marker for deposition onto the textile article in the textile manufacturing process may be performed in a variety of different ways. According to an exemplary embodiment, forming the solution comprising the nucleic acid marker may include the step of mixing the unique nucleic acid sequence with a first media that is liquefied in a solvent. The solution comprising the nucleic acid marker may then be applied to the textile. The first media may solidify after the evaporation of the solvent component of the solution.

According to an exemplary embodiment of the present invention, the nucleic acid marker may be mixed with a water insoluble media to generate the solution comprising the nucleic acid marker. The nucleic acid may be first dissolved in a water soluble solution. Then the water insoluble media may be dissolved in a solvent. An intermediate solution may then be used to mix the water soluble solution having the nucleic acid marker with the water insoluble media. The resulting solution comprising the nucleic acid marker may then be applied to the textile.

According to an exemplary embodiment of the invention, a method to deposit the nucleic acid marker on the article may include activating the nucleic acid marker and/or activating at least a portion of the surface of the article onto which the nucleic acid marker is deposited. The nucleic acid marker alone may be activated, or the surface of the article may be activated or both the nucleic acid marker and the surface of the article may be activated. By way of example and not of limitation, an activated site on the nucleic acid marker may be generated which reacts with cellulose (cotton fiber, etc.). The activated site on the nucleic acid marker may also react with nylon, certain polyesters, wool, or other fiber types.

Figure 3:
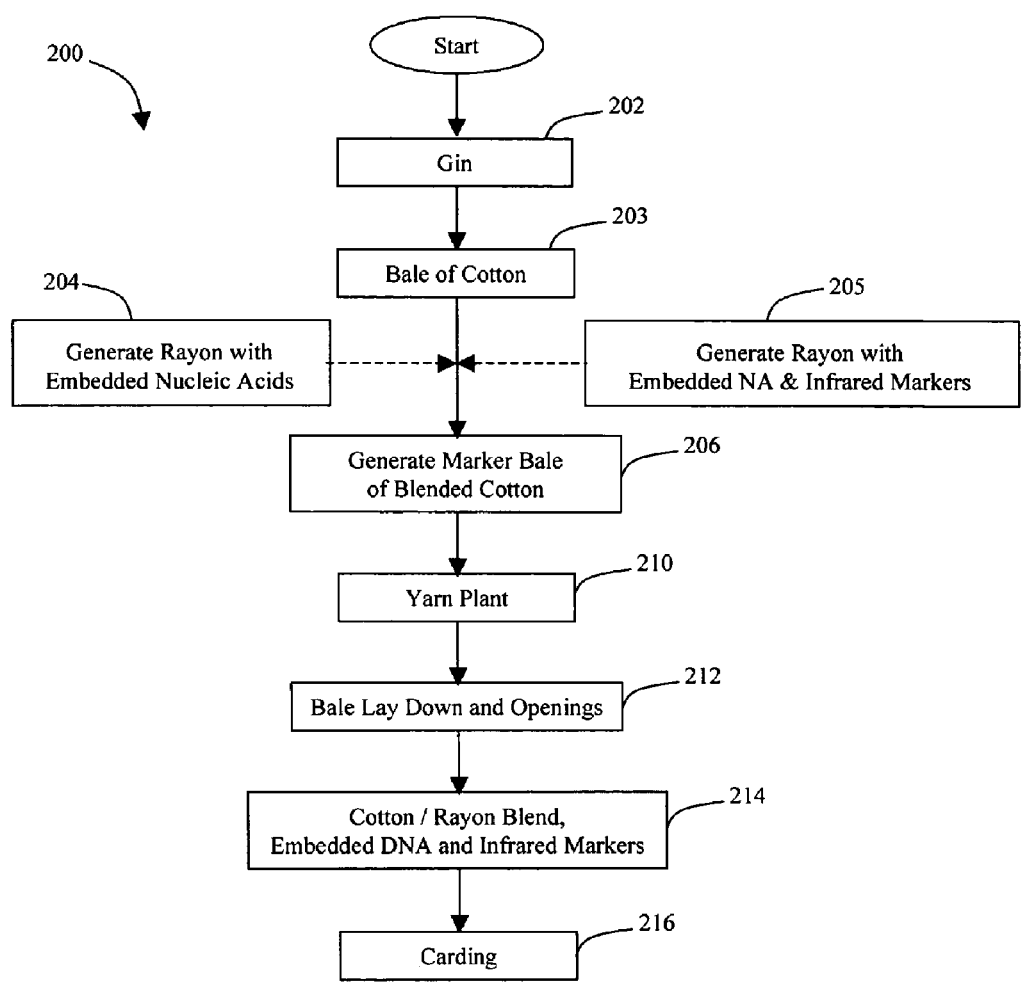
FIG. 3 is a flowchart of an illustrative method for depositing a nucleic acid marker onto a fibrous material.

FIG. 3 is a flowchart of an illustrative method for depositing a nucleic acid marker onto a fibrous material. Referring to FIG. 3 a method 200 for depositing the nucleic acid marker onto a fibrous material is illustrated. The solution comprising the nucleic acid marker may be embedded into fibrous materials during the manufacturing of the fibers or fibrous materials. The method 200 is initiated at block 202 in which a gin is used to separate cotton fibers from cotton seed. The method then proceeds to block 203 in which a bale of cotton is produced. At block 204, the nucleic acid marker may be embedded into a fiber such as rayon. The nucleic acid marker may be embedded into the illustrative rayon fiber along with an optical reporter, such as an infrared marker, as described in block 205. The nucleic acid marker may be embedded into the fibers or fibrous materials using additional processing equipment, chemistry, and conditions as necessary.

The rayon may be blended with cotton from the bale of cotton to generate a marker bale of blended cotton as described in block 206. The resulting "blend" may be an intimate mixture of fibers of different generic type, composition, length, diameter, or color spun together in one yarn. In intimate blends, both fibers may be present in the same yarn in desired proportions. Fiber types might not be readily separated when they are next to each other throughout the yarn. The method then proceeds to block 210 in which the marker bale is then received by a yarn plant. The bale proceeds to the lay down and opening process in block 212. Opening may be an initial step in the production of spun yarns which loosens fibers from the bale and cleans and blends the fibers. The marked cotton fibers may be referred to as "marked fibers" and may be combined with other cotton fibers to generate a blend of combined cotton that can be identified using the nucleic acid markers embedded therein. The illustrative method then proceeds to the carding process in block 216. During carding stable fibers may be drawn together in a substantially parallel arrangement to form a weak rope of fibers referred to as a "carded sliver." After carding, the fibers or fibrous materials that have been marked with the nucleic acid markers may be combined to produce a yarn, thread, fabric, nonwoven fabric, or any product made using fibrous materials. By way of example and not of limitation, the illustrative yarn containing the nucleic acid markers may be combined with one or more yarns that do not contain nucleic acid markers. The resulting product may be identified by the presence of the nucleic markers in the embedded rayon from block 204 and block 205.

Figure 4:
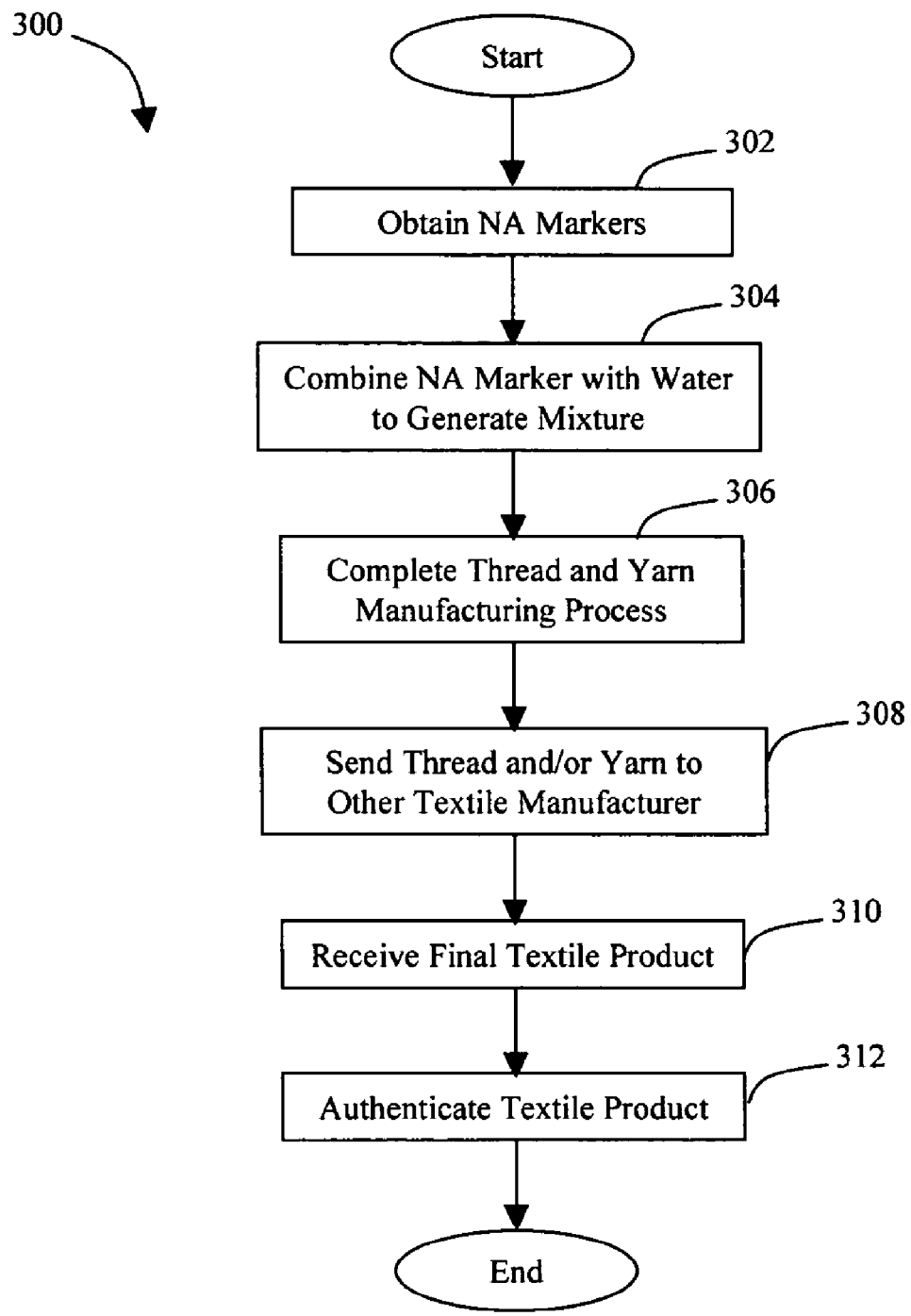
FIG. 4 is a flowchart of an illustrative method for depositing a nucleic acid marker to identify the origin of a yarn and/or thread.

FIG. 4 is a flowchart of an illustrative method for depositing a nucleic acid marker to identify the origin of a yarn and/or thread. Referring to FIG. 4, a method 300 is illustrated for applying a nucleic acid marker to identify the origin of a yarn and/or thread. The method is initiated at block 302 in which the nucleic acid markers are obtained. The nucleic acid markers may be associated with a particular manufacturer or a particular product. Using one of the methods described herein, the nucleic acid marker may be combined with a media such as water or an aqueous buffer to generate the solution comprising the nucleic acid marker.

During the thread and yarn manufacturing process of block 306, the solution comprising the nucleic acid marker may be sprayed onto the cotton fiber during the bale opening process to form a marked cotton fiber (e.g., a marked thread and/or yarn).

At block 308, the marked thread and/or yarn may be sent to a textile manufacturer for further processing. At block 310, a finished textile is received. At block 312, the authentication methods described herein may be used to confirm that the marked cotton thread and/or yarn was manufactured using the marked thread and/or yarn. For example, the authentication of the marked textile may include determining whether the final textile product includes textile materials from a particular country or region.

Figure 5:
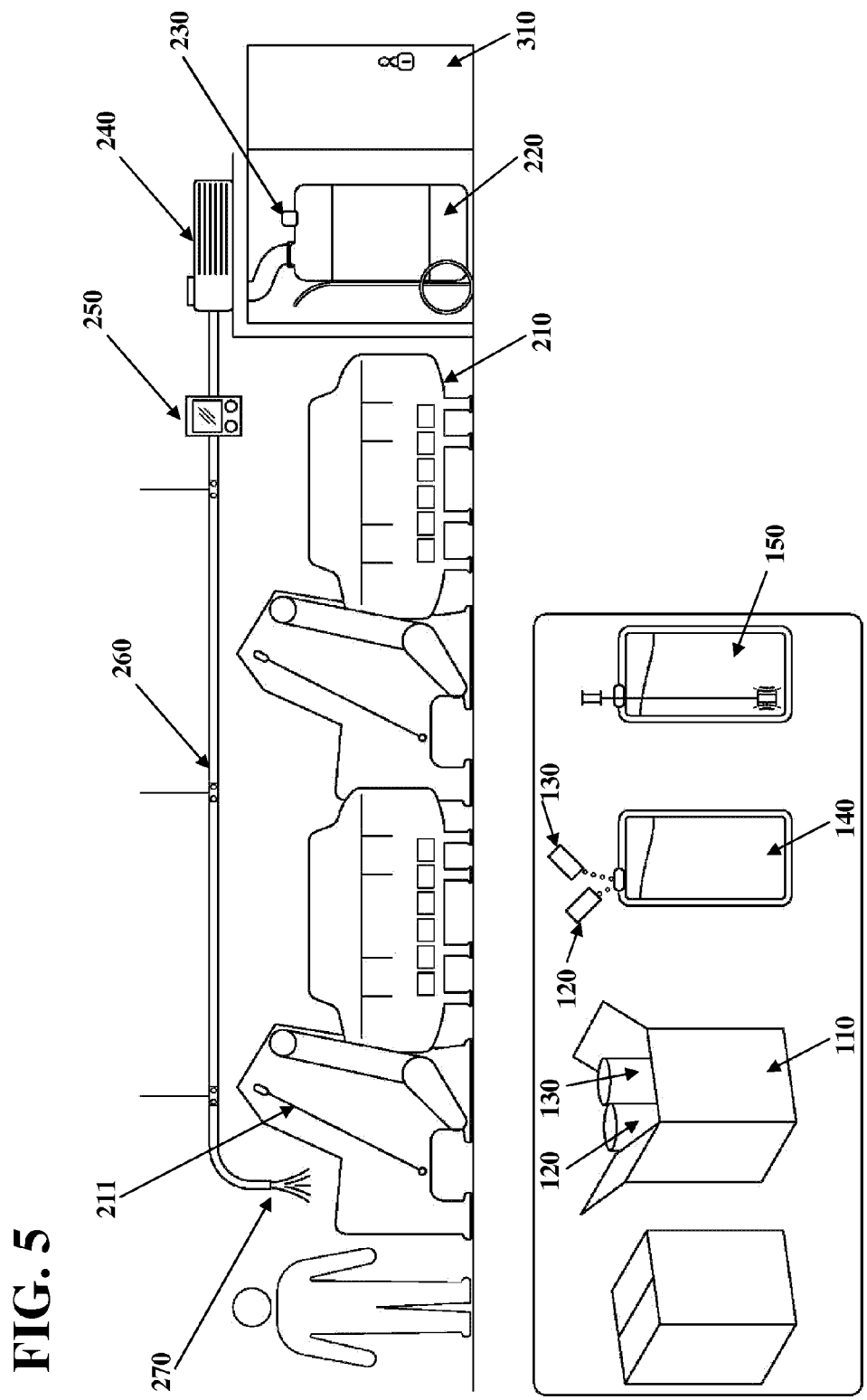
FIG. 5 illustrates a method for depositing a nucleic acid marker onto an article and a device configured to apply the method of depositing the nucleic acid marker onto the article according to exemplary embodiments of the present invention.

FIG. 5 illustrates a method for depositing a nucleic acid marker onto an article and a device configured to apply the method of depositing the nucleic acid marker onto the article according to exemplary embodiments of the invention. With reference to FIG. 5, according to an exemplary embodiment of the present invention, the device for marking the article may be configured to apply the nucleic acid marker to a raw textile material (e.g., raw cotton fibers or raw wool fibers) during ginning by spraying the solution comprising the nucleic acid marker onto the raw textile material. The device for marking the textile article may be used in conjunction with an automated ginning machine including one or more conveyor belts 211 and one or more scouring bowls 210 connected in series and configured to scour the raw textile material. The device for marking the textile may be configured to apply the solution comprising the nucleic acid marker to the raw textile material during scouring of the raw textile material. The raw textile material may be any raw textile material, for example, raw wool or raw cotton.

The device for marking the textile may include a reservoir barrel 220 storing the solution comprising the nucleic acid marker, a pump 240, a metering control 250, a delivery mechanism 260 and one or more outlets 270. The device may include an indicator 230 operatively connected to the reservoir barrel 220 and configured to indicate when an amount of the solution comprising the nucleic acid marker in the reservoir barrel 220 is low. The reservoir barrel 220 may be stored in a lockable space 310 configured to record the time and identity of anyone accessing the lockable space.

The reservoir barrel 220 may be of any desired size or dimensions suitable for holding the desired amount of nucleic acid marker mixture. The size of the reservoir barrel 220 may be determined based on the amount of nucleic acid marker mixture desired to be held. For example, the size of the reservoir barrel 220 may be selected in order to continuously spray the solution comprising the nucleic acid marker onto the article for a desired period of time. The size of the reservoir barrel 220 may be determined based on the amount of raw textile material to be marked. For example, the reservoir barrel 220 may be any suitable size, such as for instance and without limitation, a 55 gallon barrel configured to store the solution comprising the nucleic acid marker.

The indicator 230 connected to the reservoir barrel 220 and configured to indicate when the amount of nucleic acid marker mixture in the reservoir barrel 220 is low may include a visual indicator, such as, for instance, a meter, an indicator, or a light. For example, a red light may indicate the amount of nucleic acid marker mixture is low and a green light may indicate the amount of nucleic acid marker mixture is not low. In another example, a yellow light may indicate an intermediate volume of nucleic acid marker mixture.

The pump 240 may be connected the reservoir barrel 220 and may be configured to pump the solution comprising the nucleic acid marker from the reservoir barrel 220 to the delivery mechanism 260. The pump 240 may have the capacity to pump any desired amount of the solution comprising the nucleic acid marker to the delivery mechanism 260. For example, an appropriately sized pump 240 may be selected based on a desired flow rate to deposit a particular amount of the solution comprising the nucleic acid marker on the raw textile material. For example, the pump 240 may be configured to deliver an amount of the solution comprising the nucleic acid marker to mark the raw textile material in an amount of ing of DNA/kilogram of raw textile material to 1 µg of DNA/kilogram of raw textile material. The pump 240 may be configured to pump an amount of the solution comprising the nucleic acid marker to mark a raw textile material, such as for instance, raw cotton or raw wool.

Both wool and cotton have an inherent water content which contributes to the overall measured weight for processed cotton that is appropriate for textile production. During typical preparation procedures for cotton and wool, the final water content for processed cotton or wool is maintained at industry accepted levels. For example, the length and intensity of a drying process may increase or decrease the relative amount of water remaining in cotton or wool after it has been processed. The water content concentration of processed cotton that has not been marked with the solution comprising the nucleic acid marker may generally be maintained at approximately 8.5% w/w of water per total weight of cotton. The water content of processed wool that has not been marked with the solution comprising the nucleic acid marker may generally be maintained at approximately 12% w/w of water per total weight of wool. In order to mark raw textile materials such as cotton or wool with 2% w/w of the solution comprising the nucleic acid marker per total weight of raw textile material, the water content of cotton or wool may be reduced by approximately 2% w/w and may be replaced with approximately 2% w/w of the solution comprising the nucleic acid marker per total weight of raw textile material such that the standard 8.5% water content for cotton and 12% water content for wool, are maintained.

The flow rate of the pump 240 and/or a deposition rate of the delivery mechanism 260 may be controlled by any suitable means, such as for instance by a metering control unit 250. The metering control unit 250 may be positioned at any desired location. For example, the metering control unit 250 may be positioned adjacent to the pump 240 or near the one or more outlets 270 of the delivery mechanism 260. The metering control unit 250 may control the flow rate of the solution comprising the nucleic acid marker to or through the delivery mechanism 260. The metering control unit 250 may control the amount of the solution comprising the nucleic acid marker exiting each of the one or more outlets 270 of the delivery mechanism 260. Thus, the metering control unit 250 may control the deposition rate of the solution comprising the nucleic acid marker onto the raw textile material and may therefore control the amount of nucleic acid used to mark a particular raw textile material.

The delivery mechanism 260 may include one or more outlets 270. The one or more outlets 270 may be positioned at any location along the delivery mechanism 260. For example, the one or more outlets 260 may be positioned to discharge the solution comprising the nucleic acid marker as a mist over the raw textile material being conveyed through a ginning machine or scouring bowls 210. The scouring bowls 210 may carry the raw textile material to an elevated point along on or more angled conveyor belts 211 and allow the raw textile material to fall to a subsequent component of the scouring bowls 210. This process may be carried out as part of scouring or ginning the raw textile material. The one or more outlets 270 may be positioned to discharge the solution comprising the nucleic acid marker onto the raw textile material at the point where the raw textile material is allowed to fall to the subsequent scouring bowl 210.

According to exemplary embodiments of the invention, the nucleic acid marker solution may be pumped out of the reservoir barrel 220 and into the delivery mechanism 260. The nucleic acid marker solution may be pumped through the delivery mechanism 260 to the one or more outlets 270. The nucleic acid marker solution may then be sprayed onto the raw textile material through the one or more outlets 270.

According to an exemplary embodiment of the invention a concentrated nucleic acid marker 120 and an alkali activator 130 may be provided at step 110. The concentrated nucleic acid marker 120 and the alkali activator 130 may be added to water at step 140 and the resulting solution may be agitated at step 150 to form an activated solution comprising the nucleic acid marker. The activated solution comprising the nucleic acid marker may then be transferred to the reservoir barrel 220 for use. A pre-activated solution comprising the nucleic acid marker may also be provided in a reservoir barrel 220.

Figure 6:
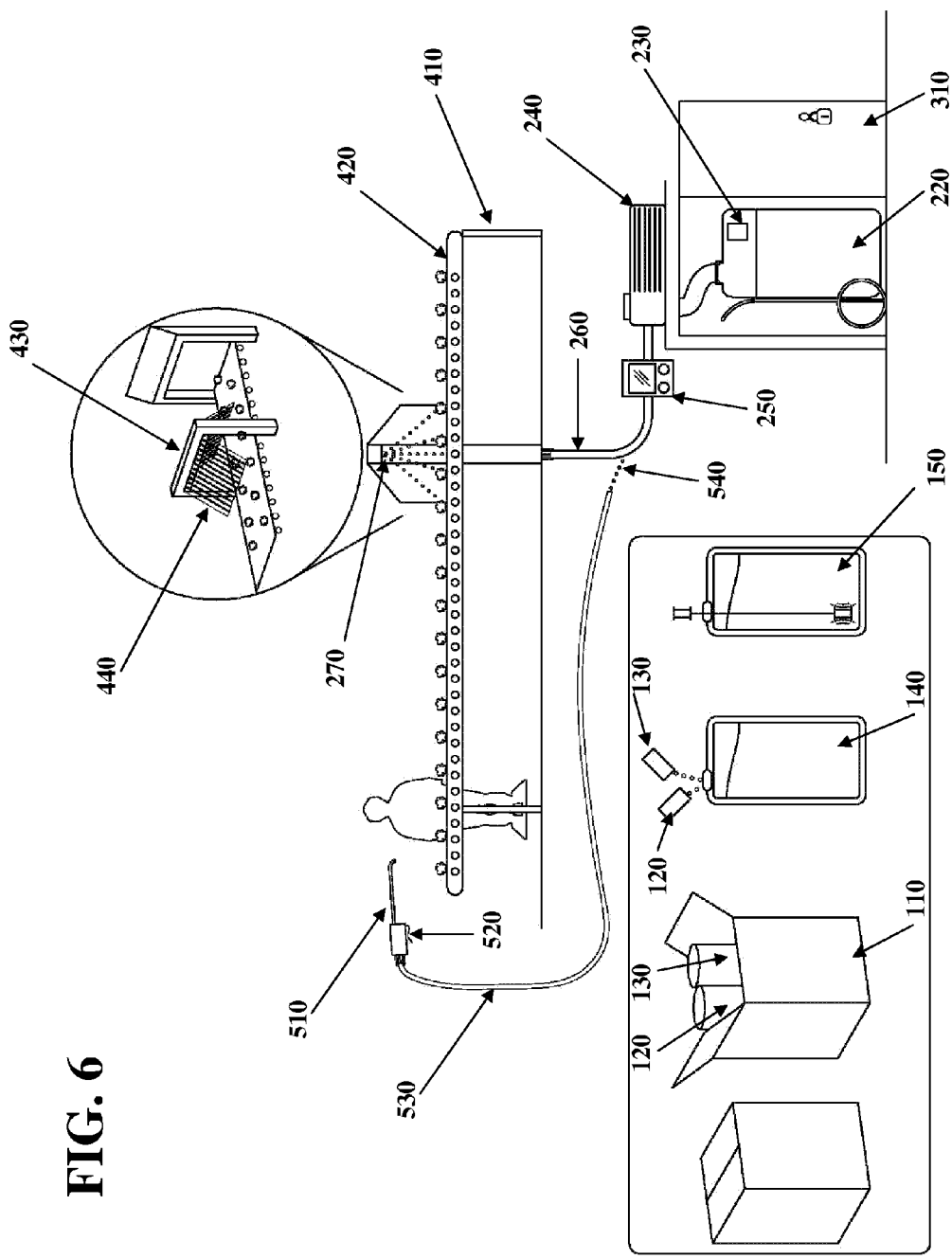
FIG. 6 illustrates a method for depositing a nucleic acid marker onto an article and a device configured to apply the method of depositing the nucleic acid marker onto the article according to exemplary embodiments of the present invention.

FIG. 6 illustrates a method for depositing a nucleic acid marker onto an article and a device configured to apply the method of depositing the nucleic acid marker onto the article according to exemplary embodiments of the invention. Except where otherwise indicated, the device and method illustrated in FIG. 6 are substantially the same or similar to the device and method discussed with reference to FIG. 5. With reference to FIG. 6, according to an exemplary embodiment of the invention, the device for marking the article may be configured to apply the solution comprising the nucleic acid marker onto the raw textile material during picking/cleaning of the raw textile material by spraying the solution comprising the nucleic acid marker onto the raw textile material. The device for marking the textile article may be used in conjunction with a picking/cleaning line machine 410 including one or more conveyor belts 420 and may be configured to allow picking/cleaning of the raw textile material. The device for marking the textile may be configured to apply the solution comprising the nucleic acid marker onto the raw textile material during picking/cleaning of the raw textile material. The raw textile material may be any raw textile material, for example, wool or cotton.

The delivery mechanism 260 may include one or more spray bars 430 holding the one or more outlets 270 of the delivery mechanism 260. The spray bars 430 may be suspended over the conveyor belt 420 of the picking/cleaning line machine 410. The spray bar 430 may include a shroud 440 configured to prevent the solution comprising the nucleic acid marker from being sprayed in an area outside of the conveyor belt 420. The shroud 440 may be of any desired size or dimensions suitable for preventing the solution comprising the nucleic acid marker from being sprayed in the area outside of the conveyor belt 420. For example, the shroud 420 may have a pyramid shape including two shielding elements extending at a downward angle from the spray bar.

According to an exemplary embodiment of the invention, the device may include a manual applicator 510 configured to be manually operated by a person positioned along the conveyor belt 420. The manual applicator 510 may include an on/off switch or a discharge lever 520 configured to activate the manual applicator 510. The manual applicator 510 may be configured to discharge the solution comprising the nucleic acid marker at any point along the conveyor belt 420. The manual applicator 510 may include a delivery hose 530 connected to the pump 240 and/or the metering control 250. The manual applicator 510 may include a quick disconnect component 540 configured to attach and/or release the delivery hose 530 of the manual applicator 510 to the pump 240 or the metering control 250. The manual applicator 510 may also be connected directly to the reservoir barrel 220 and may include its own pump and/or metering control.

An exemplary embodiment of the invention provides a device for marking an article including a conveyor belt adapted to convey an article in a direction of a delivery mechanism positioned at a location along the conveyor belt. The conveyor belt may be of any height, width, length or other desired dimensions to accommodate the article to be marked. The conveyor belt may be adapted to move in any desired direction. The conveyor belt may be motorized or manually operable. The conveyor belt may convey the article at a variety of speeds. The speed of the conveyor belt may be adjusted either manually or automatically. The conveyor belt may be controlled by a computer system. The conveyor belt speed may be adjusted according to, for example, a flow rate, a flow pressure or a deposition rate of the solution comprising the nucleic acid marker.

The delivery mechanism may include one or more outlets. The number of outlets may vary according to, for example, the amount of solution comprising the nucleic acid marker that is deposited on the article. The number of outlets may vary according to the size of the conveyor belt or the speed of the conveyor belt. The size of the one or more outlets may be individually and/or collectively adjustable in order to regulate, for example, the flow rate, flow pressure or a deposition rate of the solution comprising the nucleic acid marker. The position of the one or more outlets on the delivery mechanism may be adjustable so that the one or more outlets can be moved. The direction that the one or more outlets face may adjustable, for example, to adjust the direction that the solution comprising the nucleic acid marker exits the one or more outlets. The shape of the one or more outlets may be any suitable shape to output a solution comprising the nucleic acid marker. For example, the one or more outlets may be formed in a cone or cylinder shape. The one or more outlets may be adapted to provide a mist with the solution comprising the nucleic acid marker onto the article. The one or more outlets may be adapted to provide a continuous, non-continuous or intermittent spray onto the article.

The delivery mechanism may be adapted to deposit the solution comprising the nucleic acid marker through the one or more outlets onto the article and marking the article with the solution comprising the nucleic acid marker. The delivery mechanism may be positioned at any suitable region along the conveyor belt. For example, the delivery mechanism may cover a width of the conveyor belt. The delivery mechanism may be positioned at any desired angle to deposit the solution comprising the nucleic acid marker onto the article. For example, the delivery mechanism may be suspended above the conveyor belt or along the side of the conveyor belt. More than one delivery mechanism may be positioned at more than one location along the conveyor belt. The delivery mechanism may include one or more reservoirs, and the reservoirs may store the solution comprising the nucleic acid marker.

In an exemplary embodiment of the invention, the one or more outlets may be disposed on a spray bar positioned to deliver the solution comprising the nucleic acid marker onto the article. The spray bar may be adapted to deposit the solution comprising the nucleic acid marker through the one or more outlets onto the article and marking the article with the solution comprising the nucleic acid marker. The spray bar may be positioned at any region of the platform of the conveyor belt. The spray bar may be positioned at any desired angle to deposit the solution comprising the nucleic acid marker on the article. More than one spray bar may be positioned at more than one location along the conveyor belt. The spray bar may be operatively linked to one or more reservoirs, and the reservoirs may store the solution comprising the nucleic acid marker.

In an exemplary embodiment of the invention, the device for marking an article may include a regulator (e.g., the metering control shown in FIGS. 6 and 7) associated with the delivery mechanism. The regulator may be adapted to regulate an amount of the solution comprising the nucleic acid marker deposited by the delivery mechanism through the one or more outlets. The regulator may also be at any desired position associated with the delivery mechanism to regulate the amount of solution comprising the nucleic acid marker deposited. For example, the regulator may be positioned along a stream of the solution comprising the nucleic acid marker exiting the delivery mechanism. The regulator may regulate, for example, a flow rate, a flow pressure or a deposition rate of the solution comprising the nucleic acid marker. The regulator may be adjusted manually or automatically. The regulator may be automated, for example, by being monitored and/or adjusted by a computer system.

The regulator may regulate, for example, a flow rate, a flow pressure or a deposition rate of the solution comprising the nucleic acid marker at each individual outlet or may regulate all of the one or more outlets simultaneously. The regulator may regulate the deposition rate of the solution comprising the nucleic acid marker according to the rate of the conveyor belt. For example, if the conveyor belt is moving at a slower relative speed, then the regulator may adjust the deposition rate of the solution comprising the nucleic acid marker to be slower. For example, if the conveyor belt is moving at a relatively high speed, then the regulator may adjust the deposition rate of the solution comprising the nucleic acid marker to keep up with the rate of the conveyor belt. The regulator may be used to adjust the deposition rate of the nucleic acid marker solution appropriate for the number or amount of the articles placed on the conveyor belt.

The regulator may regulate a deposition rate of the solution comprising the nucleic acid marker to achieve a desired water content concentration of the article by regulating an amount of the solution comprising the nucleic acid marker (e.g., an aqueous solution) deposited onto the article. For example, the water content concentration of processed cotton that has not been marked with the solution comprising the nucleic acid marker may generally be maintained at approximately 8.5% w/w of water per total weight of cotton. The water content of processed wool that has not been marked with the solution comprising the nucleic acid marker may generally be maintained at approximately 12% w/w of water per total weight of wool.

In an exemplary embodiment of the invention, the device for marking an article may include a measurement apparatus associated with the delivery mechanism. The measurement apparatus may be adapted to measure an amount of the solution comprising the nucleic acid marker deposited by the delivery mechanism. The measurement apparatus may be located at any desired position associated with the delivery mechanism to measure the amount of solution comprising the nucleic acid marker deposited by the delivery mechanism through the one or more outlets. For example, the measurement apparatus may be positioned along a stream of the solution comprising the nucleic acid marker exiting the delivery mechanism. The measurement apparatus may measure, for example, a flow rate, a flow pressure or a deposition rate of the solution comprising the nucleic acid marker. The measurement apparatus may measure, for example, the flow rate of the solution comprising the nucleic acid marker through an individual outlet. The measurement apparatus may be manually or automatically controlled. The measurement apparatus may be controlled by a computer system. The measurement apparatus may provide a signal to the regulator to allow the regulator to adjust the deposition rate of the solution comprising the nucleic acid marker. The measurement apparatus may provide a signal to the regulator to adjust the deposition rate of the solution comprising the nucleic acid marker onto the article to maintain the desired water content concentration. A computer system may be used to monitor and control the regulator and the measurement apparatus.

Authentication of a Marked Article

The nucleic acid marker may be used to identify specific characteristics of an article. For example, the nucleic acid marker may be used to determine whether or not a particular article of interest is authentic by determining whether the article of interest is marked with the nucleic acid marker. By way of example and not of limitation, the nucleic acid marker may be used to encode product information, such as, country of origin for the textile material, origin of the final product, information about the manufacturer, plant identification, product identification and anyt other desired or related data. The presence of the nucleic acid marker in the article may be identified or tracked at any point in the stream of commerce.

The presence of the nucleic acid marker in an article of interest may be detected by using portable scanners and/or lab verification methods that may include for instance PCR or isothermal amplification followed by any suitable specific marker sequence detection method, such as for instance specific amplicon size detection, or specific marker sequence detection by hybridization with a sequence specific probe. By way of example and not of limitation, test kits, portable scanners and lab verification may be purchased and/or performed by any commercially available source, such as for instance, New England BioLabs®, Inc. (Ipswich, Mass.).

According to exemplary embodiments of the invention, the identification data for each nucleic acid marker may be stored in a database. This database may store a plurality of product information, as described above.

Wool obtained by shearing a sheep, contains a high level of lanolin (wool wax or wool grease), as well as dead skin, sweat residue, pesticides, and other material such as dirt and vegetable matter. Before the wool can be used for commercial purposes, it is scoured, a process of cleaning the greasy wool. Scouring may be accomplished simply by immersion in a bath of warm water or by an industrial process using detergent and alkali in specialized equipment.

Figure 7:
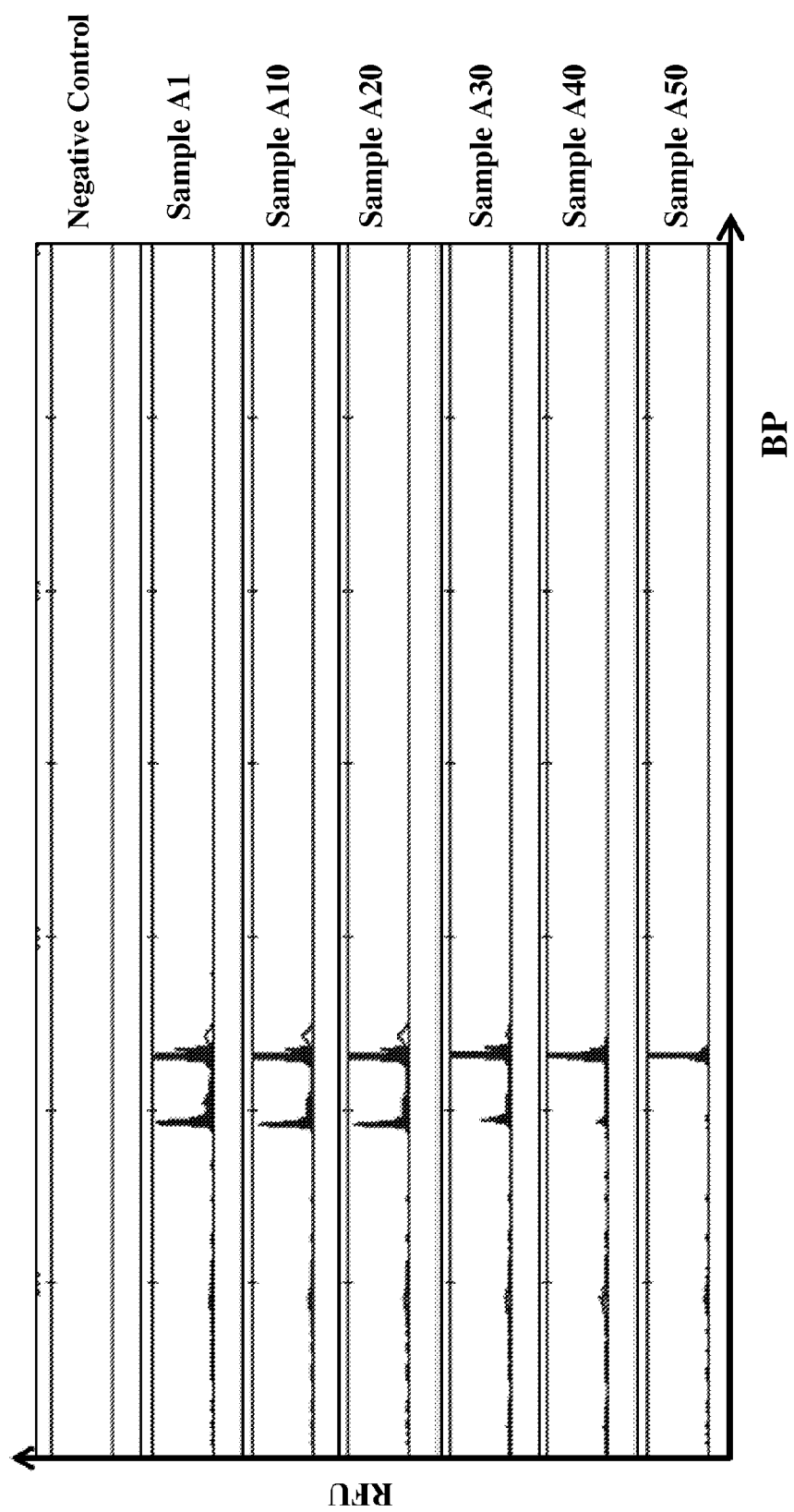
FIG. 7 shows authentication data from capillary electrophoresis traces of PCR products from marked raw wool.

In a test of DNA (SigNature® T DNA, Applied DNA Sciences, Inc., Stony Brook, N.Y.) marking of raw wool, alkaline activated double stranded marker DNA was added to a graduated reservoir barrel of 450 L unheated water filled from the local water supply and stirred to mix the aqueous DNA marker solution to achieve a concentration in a range from about 0.1 pg/ml to about 1 ug/ml. The DNA was deposited onto raw wool in the scouring step as in 101a of FIG. 2. A 3,000 kg batch of raw wool (Batch A) was separated from a bale and the separated loose fiber was passed along a conveyor belt under a sprayer depositing the aqueous DNA marker solution from the graduated barrel at a rate of approximately 70 L/hr with the aim of depositing 20 ml per kg raw wool. After an initial 45-60 minutes of spraying, the rate of deposition of the aqueous DNA marker solution was estimated to be higher than the desired 20 ml per kg, so the aqueous DNA marker solution was supplemented with 50 L water and mixed again. Approximately 120 L of this supplemented aqueous DNA marker solution was used to spray the remainder of the 3,000 kg of raw wool. Fifty aliquots of the sprayed raw wool were taken at 2 min. intervals and labeled serially A1 to A50. Samples from each aliquot were sent to Applied DNA Sciences, Inc., where they were subjected to PCR with a primer pair complementary to the two strands of the marker DNA. Amplified products were separated by capillary electrophoresis and demonstrated detectable marker DNA at all time-points tested. (See FIG. 7 showing the results for every tenth sample A1-A50).

Figure 8:
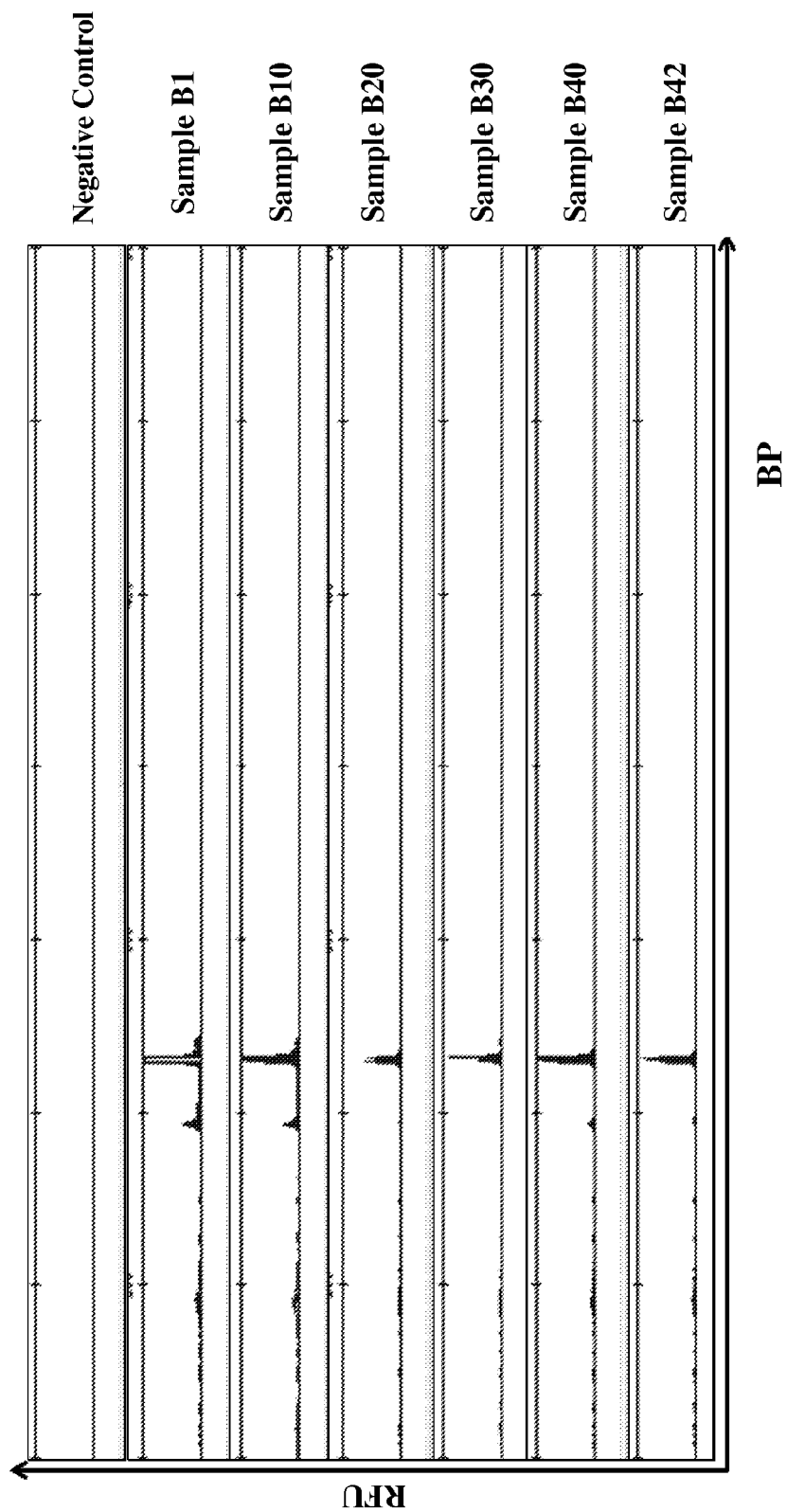
FIG. 8 shows authentication data from capillary electrophoresis traces of PCR products from marked raw wool.

The remaining supplemented aqueous DNA marker solution was bought up to a volume of 450 L again by the addition and mixing of water and 200 L of this second supplemented aqueous DNA marker solution was deposited on a second batch of raw wool of 5,000 kg (Batch B). Fifty aliquots of the sprayed raw wool were taken at 5 min. intervals and labeled serially B1 to B50. Samples from each aliquot were subjected to PCR as before. Amplified products were separated by capillary electrophoresis and demonstrated detectable marker DNA at all time-points tested. (See FIG. 8 showing the results for samples B1-B42).

The remaining second supplemented aqueous DNA marker solution was again bought up to a volume of 450 L again by the addition and mixing of 200 L water; and this third supplemented aqueous DNA marker solution was used to deposit marker DNA on a third batch of raw wool of 25,000 kg at a rate of approximately 50 L/hr to mark the first portion of the third batch of raw wool (Batch C). After 2 hrs of spraying, the volume of the third supplemented aqueous DNA marker solution was again made up to 450 L with water and mixed to form the fourth supplemented aqueous DNA marker solution, which was used to continue spraying Batch C for 2 hours at the same rate of spray deposition onto the raw wool.

Figure 9:
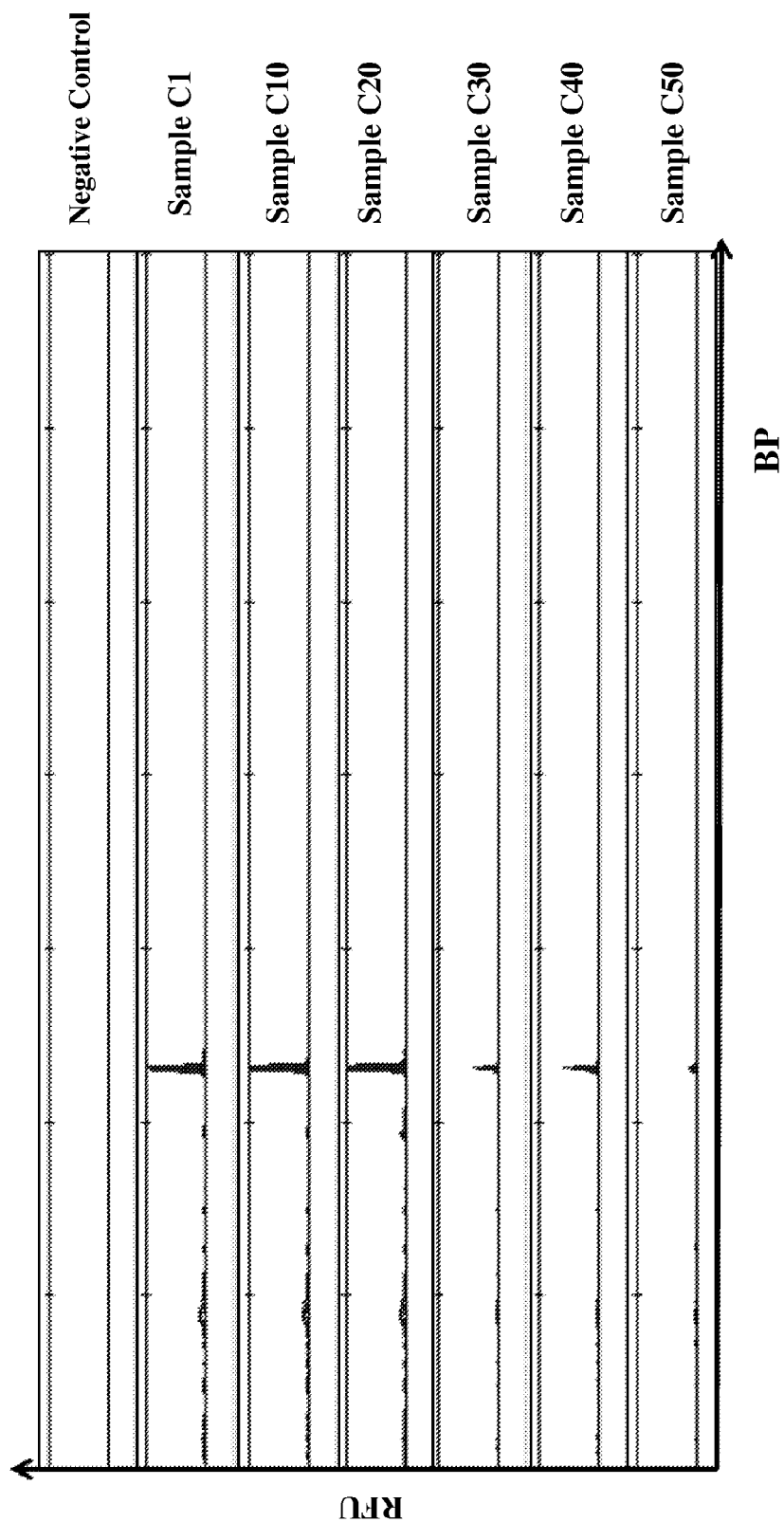
FIG. 9 shows authentication data from capillary electrophoresis traces of PCR products from marked raw wool.

The process of supplementing the previously supplemented aqueous DNA marker solution to make up the volume to 450 L and mixing, followed by spraying for two hours and repeating the supplementing and mixing and spraying process was repeated twice more and the last 450 L was used to mark the remainder of the 25,000 kg of the separated bale of Batch C. Fifty aliquots of the sprayed raw wool were taken at 15 min. intervals and labeled serially C1 to C50. Samples from each aliquot were subjected to PCR as before. Amplified products were separated by capillary electrophoresis and demonstrated detectable marker DNA at all time-points tested. FIG. 9 shows results for samples C1-050 demonstrating that less of the amplified DNA was detected in the fibers marked with the most diluted marker DNA solutions.

Figure 10:
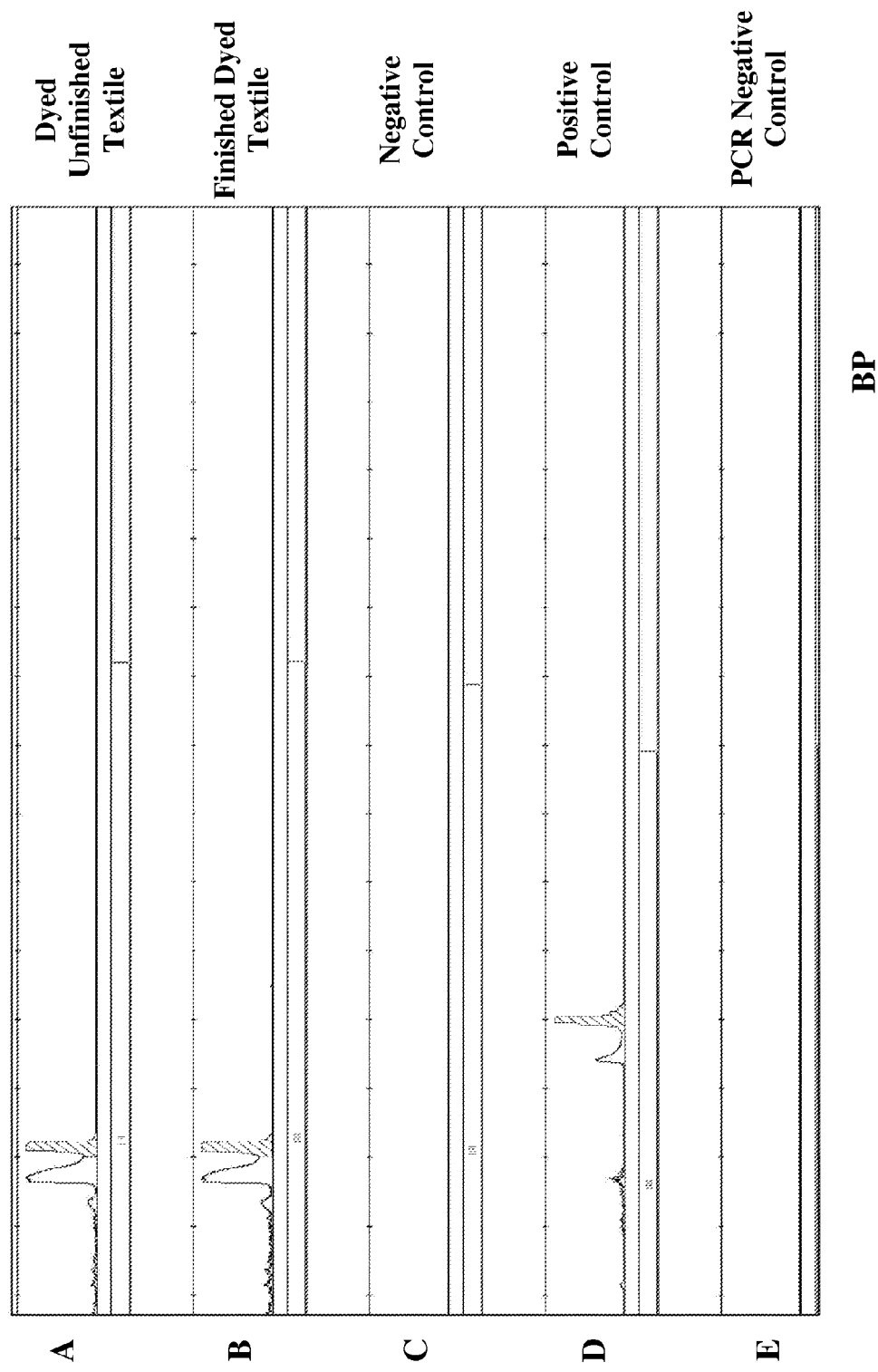
FIG. 10 shows authentication data from capillary electrophoresis traces of PCR products from unfinished and finished textile articles.

FIG. 10 shows authentication data from samples from a finished and an unfinished textile article marked with a SigNature® T DNA marker essentially as described above after the dying step as in 101f of FIG. 2. The X axis represents a number of base pairs (BP) and the Y axis represents relative fluorescence units (RFU). In FIG. 10, the shaded peak in lane A indicates the presence of a nucleic acid marker (e.g., DNA) was detected in an unfinished textile article. The shaded peak in lane A indicates that multiple copies of a specific amplicon copied by PCR from the nucleic acid marker (e.g., in this case DNA) was detected. The shaded peak in lane B indicates the presence of the same nucleic acid marker as in lane A in a finished textile article. The shaded and unshaded peaks in lanes A and B are substantially similar in size, which indicates qualitatively similar amounts of nucleic acid marker were present in both the finished and unfinished textile articles. Lane C represents a negative control in which the textile had not been marked with the nucleic acid marker. The absence of a peak in lane C indicates that a false positive result has not been detected. Lane D represents a PCR positive control. The peaks in lane D are at a different position than the peaks in lanes A and B because the PCR positive control employed a different DNA sequence having a different number of base pairs than the nucleic acid marker identified in lanes A and B, but demonstrate that the PCR amplification successfully copied amplicons from the control DNA sequence. The presence of the peak in lane D indicates that the PCR reaction proceeded as expected. The lack of a peak in lane E serves as a negative PCR control and further indicates that the PCR reaction was dependent on DNA marker.

Figure 11:
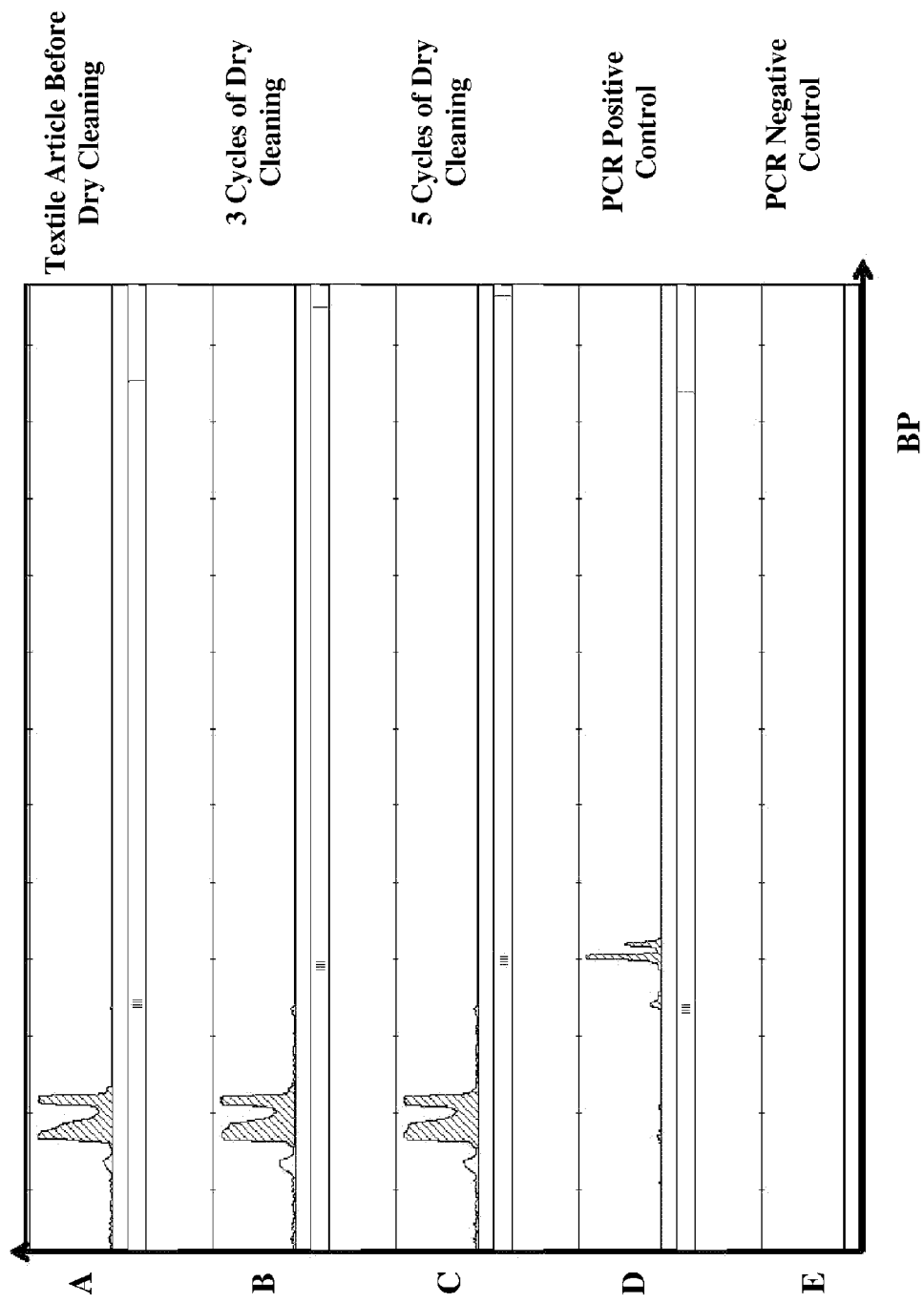
FIG. 11 shows authentication data from capillary electrophoresis traces of PCR products from textile articles before and after multiple cycles of dry cleaning the textile articles.

FIG. 11 shows authentication data from samples from DNA-marked textile articles produced essentially as described above, before and after multiple cycles of dry cleaning the textile articles. The X axis represents a number of base pairs (BP) and the Y axis represents relative fluorescence units (RFU). With reference to FIG. 11, the shaded peak in lane A indicates the presence of a nucleic acid marker (e.g., DNA) was detected in a textile article before dry cleaning. The shaded peak in lane B indicates the presence of the nucleic acid marker was detected after 3 cycles of dry cleaning. The shaded peak in lane C indicates the presence of the nucleic acid marker was detected after 5 cycles of dry cleaning. The shaded peaks in lanes B and C have substantially the same size and position, which indicates that the same nucleic acid marker (i.e., a nucleic acid having the same number of base pairs (BP) is identified) is present in the samples tested in lanes B and C as in lane A, and the nucleic acid marker is present in substantially the same amount as in lane A. Thus, dry cleaning does not reduce the amount of nucleic acid marker present in a marked textile article. Lane D represents a PCR positive control. The peaks in lane D are at a different position than the peaks in lanes A, B and C because the PCR positive control employed a different DNA sequence having a different number of base pairs than the nucleic acid marker identified in lanes A, B and C. The presence of the peak in lane D indicates that the PCR reaction proceeded as expected. The lack of a peak in lane E serves as a negative PCR control and further indicates that the PCR reaction was dependent on DNA marker.

Figure 12:
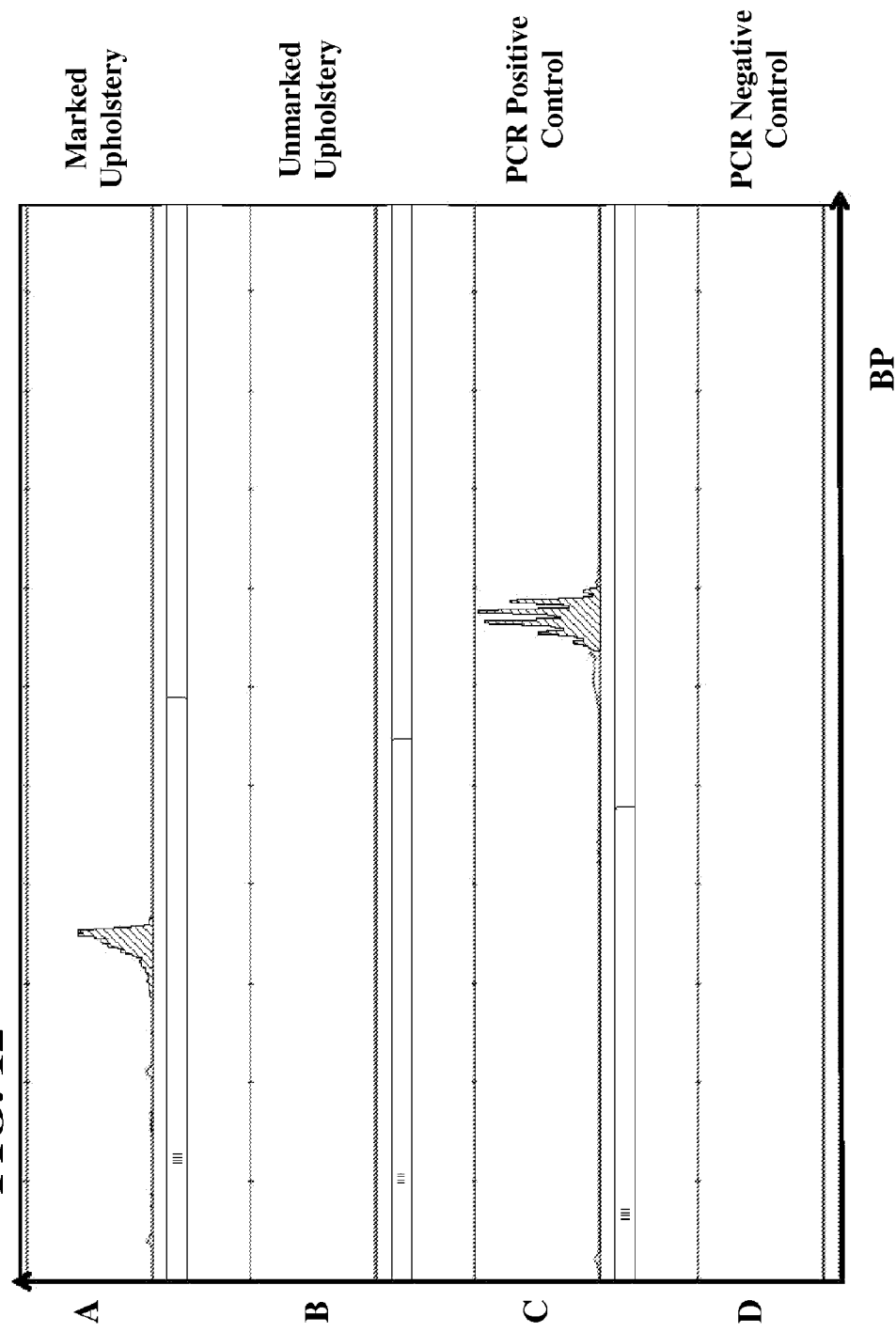
FIG. 12 shows authentication data from capillary electrophoresis traces of PCR products from an upholstery textile made from fibers marked with a nucleic acid marker.

FIG. 12 shows authentication data from capillary electrophoresis traces of PCR products from an upholstery textile marked with a nucleic acid marker prepared essentially as described above. The X axis represents a number of base pairs (BP) and the Y axis represents relative fluorescence units (RFU). With reference to FIG. 12, the shaded peak in lane A indicates the presence of the nucleic acid marker (i.e., DNA) was detected in a sample of marked upholstery after a typical finishing process to prepare upholstery for commercial sale. Lane B represents a test for the presence of the nucleic acid marker in an unmarked upholstery sample to serve as a negative control. The absence of a peak in lane B indicates that a false positive result has not been detected. Lane C represents a PCR positive control. The peaks in lane C are at a different position than the peaks in lane A because the PCR positive control employed a different DNA sequence having a different number of base pairs than the nucleic acid marker identified in lane A. The presence of the peak in lane C indicates that the PCR reaction proceeded as expected. The lack of a peak in lane D serves as a negative PCR control and further indicates that the PCR reaction proceeded as expected.

Figure 13:
FIG. 13 shows authentication data from capillary electrophoresis traces of PCR products from carpet made from fibers marked with a nucleic acid marker.

FIG. 13 shows authentication data from capillary electrophoresis traces of PCR products from carpet marked with a nucleic acid marker prepared essentially as described above. The X axis represents a number of base pairs (BP) and the Y axis represents relative fluorescence units (RFU). In FIG. 13, the shaded peak in lane B indicates the presence of the nucleic acid marker (i.e., DNA) was detected in a sample of marked carpet after a typical finishing process to prepare a carpet for commercial sale. Lane A represents a test for the presence of the nucleic acid marker in an unmarked carpet sample to serve as a negative control. The absence of a peak in lane A indicates that a false positive result has not been detected. Lane C represents a PCR positive control. The peaks in lane C are at a different position than the peaks in lane A because the PCR positive control employed a different DNA sequence having a different number of base pairs than the nucleic acid marker identified in lane B. The presence of the peak in lane C indicates that the PCR reaction proceeded as expected. The lack of a peak in lane D serves as a negative PCR control and further indicates that the PCR reaction proceeded as expected.

Similar results of DNA marking tests were demonstrated with DNA marking of wool during the roving process showing detection of specific PCR amplicon products of lengths characteristic of the marker DNA. (A roving is a long and narrow bundle of fiber. Rovings are produced during the process of making spun yarn from wool fleece, raw cotton, or other fibers). Likewise, testing of processed wool after dying with a light blue dye yielded readily detectable characteristic PCR amplicons, showing that the alkaline activated DNA marker was distributed throughout the processed wool batches and could be detected after extensive processing of the woolen fibers or yarn. Furthermore the DNA marker was detectable by PCR and capillary electrophoresis in samples of the fibers of the final manufactured carpet products and in the upholstery fabric produced from the DNA marked woolen fibers or yarn.

In the event of a conflict between a definition herein and a definition provided in a patent or publication incorporated herein by reference, the definition provided herein is intended.

The disclosures of each of the references, patents and published patent applications disclosed herein are each hereby incorporated by reference herein in their entireties.

While the invention has been shown and described with reference to exemplary embodiments thereof, it will be understood by those of ordinary skill in the art that various changes in form and detail may be made therein without departing from the spirit and scope of the invention.

What is claimed is:

1. A method of marking raw cotton fibers with a nucleic acid molecular marker, the method comprising:
   reducing a water content of raw cotton before ginning to approximately 6.5 percent w/w;
   ginning the raw cotton to remove cotton fibers from plant material to create raw cotton fibers;
   during ginning the raw cotton, depositing approximately two percent w/w of a liquid solution comprising a nucleic acid molecular marker and water onto the raw cotton fibers via misted spray of the liquid solution.

2. The method as defined in claim 1, wherein the liquid solution includes an alkaline activator and the molecular marker is a nucleic acid molecular marker and the activator aids in bonding of the nucleic acid molecular marker to the raw cotton fibers.

3. The method as defined in claim 2, wherein the alkaline activator includes a solution of a hydroxide of an alkali metal and the alkali metal is selected from the group consisting of lithium (Li), sodium (Na), rubidium (Rb), and cesium (Cs).

4. The method as defined in claim 1, including
   the depositing of the nucleic acid molecular marker being performed with a delivery mechanism comprising one or more outlets, wherein the nucleic acid molecular marker comprises alkaline activated DNA, the alkaline activated DNA being produced by exposing the DNA to a solution of an alkali metal hydroxide having a concentration from about 0.001 M to about 1.0 M; and thereby marking the raw cotton fibers with the nucleic acid molecular marker, wherein the nucleic acid molecular marker is covalently bonded to the raw cotton fibers.

5. The method of as defined in claim 4, wherein an amount of the solution comprising the nucleic acid molecular marker deposited on the article is regulated by a metering control.

\* \* \* \* \*

UNITED STATES PATENT AND TRADEMARK OFFICE
CERTIFICATE OF CORRECTION

PATENT NO. : 9,963,740 B2  
APPLICATION NO. : 14/497614  
DATED : May 8, 2018  
INVENTOR(S) : Berrada et al.

Page 1 of 1

It is certified that error appears in the above-identified patent and that said Letters Patent is hereby corrected as shown below:

In the Specification

Column 5, Lines 42 & 45:  now reads "$10^{-6}$ g/m."  
should read -- $10^{-6}$ g/mL. --

Column 7, Line 26:  now reads "the double-stranded the total"  
should read -- the double-stranded total --

Column 16, Line 43:  now reads "may be connected the"  
should read -- may be connected to the --

Column 16, Line 55:  now reads "an amount of ing of DNA"  
should read -- an amount of 1 ng of DNA --

Column 18, Line 37:  now reads "the shroud 420"  
should read -- the shroud 440 --

In the Claims

Claim No. 5, Line 5:  now reads "the method of as defined"  
should read -- the method as defined --

Signed and Sealed this  
Twenty-fifth Day of September, 2018

Andrei Iancu  
*Director of the United States Patent and Trademark Office*